(12) United States Patent
Picard et al.

(10) Patent No.: US 6,943,174 B2
(45) Date of Patent: Sep. 13, 2005

(54) 6,5-FUSED BICYCLIC HETEROCYCLES

(75) Inventors: Joseph Armand Picard, Canton, MI (US); William Howard Roark, Ann Arbor, MI (US); Drago Robert Sliskovic, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 89 days.

(21) Appl. No.: 10/362,353

(22) PCT Filed: May 9, 2001

(86) PCT No.: PCT/US01/15112

§ 371 (c)(1),
(2), (4) Date: Feb. 21, 2003

(87) PCT Pub. No.: WO01/96336

PCT Pub. Date: Dec. 20, 2001

(65) Prior Publication Data

US 2004/0014759 A1 Jan. 22, 2004

Related U.S. Application Data

(60) Provisional application No. 60/211,761, filed on Jun. 14, 2000.

(51) Int. Cl.[7] .................... A61K 31/437; C07D 471/04; A61P 29/00
(52) U.S. Cl. ........................... 514/300; 546/113
(58) Field of Search ........................ 546/113; 514/300

(56) References Cited

U.S. PATENT DOCUMENTS

| | | | |
|---|---|---|---|
| 3,985,891 A | 10/1976 | Kutter et al. | |
| 4,582,837 A | 4/1986 | Hauel et al. | |
| 4,603,139 A | 7/1986 | King | |
| 4,696,931 A | 9/1987 | Hauel et al. | |
| 4,758,574 A | 7/1988 | Robertson et al. | |
| 4,904,785 A | 2/1990 | Robertson et al. | |
| 5,141,950 A | 8/1992 | Nakane et al. | |
| 5,589,482 A | 12/1996 | Thompson | |
| 5,972,980 A | 10/1999 | Cornicelli et al. | |
| 6,140,317 A | 10/2000 | Traxler et al. | |
| 6,180,636 B1 | 1/2001 | Traxler et al. | |
| 6,180,643 B1 | 1/2001 | Zablocki et al. | |
| 6,440,973 B1 | 8/2002 | Zablocki et al. | |

FOREIGN PATENT DOCUMENTS

| | | | |
|---|---|---|---|
| DE | 2 305 339 | 8/1974 | |
| DE | 23 61 757 | 6/1975 | |
| DE | 32 24 512 | 1/1984 | |
| DE | 4227791 A1 * | 2/1993 | .......... A61K/31/44 |
| EP | 0 079 083 A1 | 5/1983 | |
| EP | 09 093 593 | 11/1983 | |
| EP | 0 419 210 A1 | 3/1991 | |
| WO | WO 97/12613 | 4/1997 | |
| WO | WO 98/08847 | 3/1998 | |
| WO | WO 98/43973 | 10/1998 | |
| WO | WO 01/30778 A1 | 5/2001 | |

OTHER PUBLICATIONS

Kuhn et al. Prostaglandins & Other Lipid Mediators. 2002, 68–69:263–90.*
Kuhn H and Chan L. Current Opinion in Lipidology. 1997, 8(2):111–7.*
Whitman et al. J. Med. Chem. 2002 45:2659–2661.*
Robertson, David W., et al, "Structure–Activity Relationships of Arylimidazopyridine Cardiotonics: Discovery and Inotropic Activity of 2–[2–Methoxy–4–(methylsulfinyl)phenyl]–1H–imidazo[4,5–c]pyridine", J. Med. Chem, 1985, vol. 28, pp 717–727; XP 000577047.
Ertepinar, H., et al, "A QSAR study of the biological activities of some benzimidazoles and imidazopyridines against *Bacillus subtilis*", Eur J Med Chem, vol. 30, 1995; pp 171–175.
International Search Report for PCT/US01/15112.

* cited by examiner

*Primary Examiner*—Evelyn Mei Huang
(74) *Attorney, Agent, or Firm*—Eric J. Baude; Claude F. Purchase, Jr.

(57) ABSTRACT

The present invention provides compounds of Formula (I) wherein $Q_1$, $Q_2$, $Q_3$, $Q_4$, $Y_1$, $Y_2$, and Z are as defined in the description, and pharmaceutically acceptable salts thereof, and $C_1-C_8$ alkyl esters thereof, which are useful for the treatment of diseases responsive to the inhibition of the enzyme 15-lipoxygenase. Thus, the compounds of Formula (I) and their pharmaceuticalyl acceptable salts are useful for treating diseases with an inflammatory component, including atherosclerosis, diseases involving chemotaxis of monocytes, inflammation, stroke, coronary artery disease, asthma, arthritis, colorectal cancer, and psoriasis.

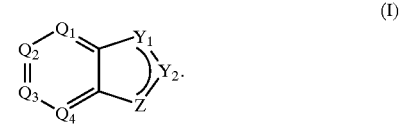

24 Claims, No Drawings

6,5-FUSED BICYCLIC HETEROCYCLES

This application claims the benefit of PCT/US01/15112 filed Sep. 5, 2001, which claims the benefit of U.S. Provisional Application 60/211,761 filed Jun. 14, 2000; the entire contents of each of which are hereby incorporated herein by reference.

FIELD OF THE INVENTION

The invention provides 6,5-fused bicyclic compounds, pharmaceutical compositions thereof, and methods of making and using such compounds and compositions to inhibit the 15-lipoxygenase enzyme, and thus treat diseases with an inflammatory component

BACKGROUND OF THE INVENTION

Hypercholesterolemia can induce monocytes to migrate into the arterial wall and mature into foam cells or tissue macrophages that accumulate fatty material, including cholesterol esters. For example, continued creation of foam cells thickens the inner lining of medium and large arteries, thereby forming atherosclerotic plaques or lesions containing cholesterol, smooth muscle cells, and connective tissue cells. Affected arteries lose elasticity and become narrowed or obstructed by the plaques. These events are the hallmark of the disease atherosclerosis. Furthermore, atherosclerotic plaques may collect calcium, become brittle, and even rupture, triggering the formation of a blood clot or thrombus capable of occluding an artery and causing a stroke or a heart attack. In addition to atherosclerosis, hypercholesterolemia plays a role in peripheral vascular diseases of small arteries, veins, and lymphatics. Thus, hypercholesterolemia may also affect the arms, legs, kidneys, and other vital organs in addition to the heart and brain.

Cholesterol is transported in blood in particles called lipoproteins, such as low-density lipoproteins. Low-density lipoproteins also contain polyunsaturated fatty acids and are necessary for foam cell formation.

Lipoxygenases are enzymes that catalyze the oxidation of polyunsaturated fatty acids and esters thereof, including those found in low-density lipoproteins. For example, the enzyme 15-lipoxygenase (15-LO) oxidizes esterified polyenoic fatty acids. 15-LO has been implicated in inflammatory disorders and in the origin and recruitment of foam cells. In addition to modifying lipoproteins involved in the formation of foam cells, 15-LO also mediates an inflammatory reaction in the atherosclerotic lesion. In human monocytes, 15-LO is induced by the cytokine IL-4.

Inhibitors of 15-LO are therefore useful to prevent and treat diseases with an inflammatory component such as asthma, psoriasis, osteoarthritis, rheumatoid arthritis, colorectal cancer, and atherosclerosis. For example, it has been shown that treatment with an inhibitor of 15-LO suppressed atherogenesis, or the production of atheroma, a fatty degeneration of the arterial wall, in rabbits fed a high-fat diet.

An object of this invention is to provide new 6,5-fused heterocycles that are potent inhibitors of 15-LO, and are thus useful for the treatment of diseases and disorders containing an inflammatory component.

SUMMARY OF THE INVENTION

The invention provides a compound of Formula I:

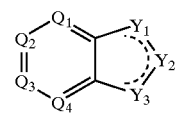

wherein:

$Q_1$, $Q_2$, $Q_3$, and $Q_4$ are independently selected from CX and N, wherein 1 or 2 of $Q_1$, $Q_2$, $Q_3$, and $Q_4$ are N; or each of $Q_1$, $Q_2$, $Q_3$, and $Q_4$ is $CH_2$ and there is a C—C double bond between the carbon atoms bearing $Q_1$ and $Y_1$, and $Q_4$ and Z, respectively, wherein X is independently selected from H, halo, hydroxy, $CF_3$, $R_1$, $OR_1$, $CO_2R_1$, $NO_2$, $NH_2$, and $SR_1$, wherein $R_1$ is H or $C_1$–$C_4$ alkyl;

is absent or a double-bond optionally between $Y_1$ and $Y_2$ when $Y_1$ and $Y_2$ are independently CH or N or between $Y_2$ and Z when $Y_2$ is CH or N and Z is CH;

one of $Y_1$ and $Y_2$ is CH, N, NH, S, or O; and the other one of $Y_1$ and $Y_2$ is C—W—Ar, wherein W is absent (in other words, a covalent bond), O, S, $NR_2$, SO, $SO_2$, CO, CHOH, $CH_2$, $NR_2CH_2$, $CH_2NR_2$, $NR_2(CO)$, or $(CO)NR_2$, wherein $R_2$ is H or $C_1$–$C_4$ alkyl, Ar is a phenyl substituted at the 3- and 4-positions relative to W, with $R_3$ and $R_4$, respectively, wherein $R_3$ is selected from H, $NHR_a$, halo, $C_1$–$C_4$ haloalkyl, COOH, —COO($C_1$–$C_6$ alkyl), (phenyl)$C_1$–$C_6$ alkoxy, hydroxy, $C_1$–$C_6$ alkoxy, —NH(CO)($C_1$–$C_6$ alkyl), nitro, and $C_1$–$C_6$ aminoalkyl, wherein $R_a$ is H, $C_1$–$C_4$ alkyl, $C_3$–$C_8$ cycloalkyl, phenyl, $C_2$–$C_6$ heteroaryl, benzyl, $CH_2$—($C_2$–$C_6$ heterocyclic radical), or -M-T, wherein M is sulfonyl, $SO_2NR_b$, $CONR_b$, $CSNR_b$, or $CSR_b$, wherein $R_b$ is H, $C_1$–$C_4$ alkyl, or $C_2$–$C_6$ heterocyclic radical, and T is $C_1$–$C_{18}$ alkyl, phenyl, or $C_3$–$C_6$ heterocyclic radical, and $R_4$ is $C_1$–$C_2$ alkoxy, $C_1$–$C_2$ thioalkoxy, hydroxy, halo, or $C_1$–$C_4$ alkyl;

Z is $NR_5$, S, O, C, or CH, wherein $R_5$ is H, [phenyl($C_1$–$C_4$ alkyl)oxycarbonyl, ($C_1$–$C_4$ alkyl)oxycarbonyl, ($C_3$–$C_8$ cycloalkyl)oxycarbonyl, ($C_3$–$C_8$ cycloalkyl)-($C_1$–$C_4$ alkyl)oxycarbonyl, or ($C_6$–$C_{10}$ aryl)oxycarbonyl;

wherein each hydrocarbyl or heterocyclic radical above is optionally substituted with between 1 and 3 substituents independently selected from halo, $C_1$–$C_4$ alkyl, $C_3$–$C_6$ cycloalkyl, $C_1$–$C_4$ alkenyl, $C_1$–$C_4$ alkynyl, phenyl, hydroxyl, amino, (amino)sulfonyl, N-acetyl, O-acetyl, $C_1$–$C_4$ thioalkyl, $C_1$–$C_4$ alkoxy, $COOR_6$, wherein $R_6$ is H or $C_1$–$C_6$ alkyl, $SO_3Na$, $SO_3H$, $SO_2NH_2$, cyano, $CH_2NH_2$, acetyl, di($C_1$–$C_4$ alkyl)amino, and nitro, wherein each substituent alkyl, cycloalkyl, alkenyl, alkynyl, or phenyl is in turn optionally substituted with between 1 and 3 substituents independently selected from halo, $C_1$–$C_2$ alkyl, hydroxyl, amino, and nitro;

and pharmaceutically acceptable salts thereof; and $C_1$–$C_8$ alkyl esters thereof.

Preferred is a compound of Formula I, and pharmaceutically acceptable salts thereof, and $C_1$–$C_8$ alkyl esters thereof, wherein $Q_4$ is N.

More preferred are compounds of Formula II

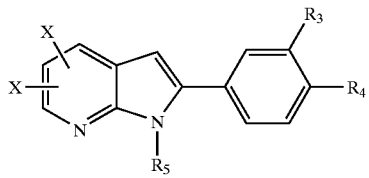

II wherein X, $R_3$, $R_4$, and $R_5$ are as defined above, and pharmaceutically acceptable salts thereof, and $C_1$–$C_8$ alkyl esters thereof.

Also preferred is a compound of Formula I, and pharmaceutically acceptable salts thereof, and $C_1$–$C_8$ alkyl esters thereof, wherein $Q_3$ is N.

More preferred are compounds of Formula III

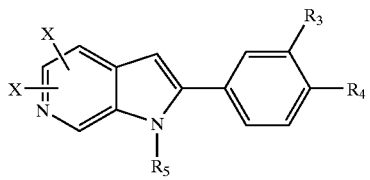

III wherein X, $R_3$, $R_4$, and $R_5$ are as defined above, and pharmaceutically acceptable salts thereof, and $C_1$–$C_8$ alkyl esters thereof.

Also preferred is a compound of Formula I, and pharmaceutically acceptable salts thereof, and $C_1$–$C_8$ alkyl esters thereof, wherein $Q_2$ is N.

More preferred are compounds of Formula IV

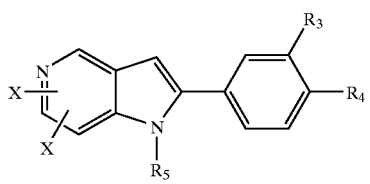

IV wherein X, $R_3$, $R_4$, and $R_5$ are as defined above, and pharmaceutically acceptable salts thereof, and $C_1$–$C_8$ alkyl esters thereof.

Also preferred is a compound of Formula I, and pharmaceutically acceptable salts thereof, and $C_1$–$C_8$ alkyl esters thereof, wherein $Q_1$ is N.

More preferred are compounds of Formula V

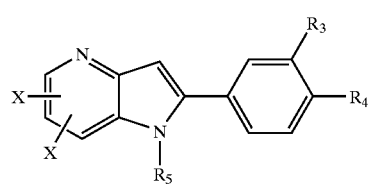

V wherein X, $R_3$, $R_4$, and $R_5$ are as defined above, and pharmaceutically acceptable salts thereof, and $C_1$–$C_8$ alkyl esters thereof.

Also preferred is a compound of Formula I, and pharmaceutically acceptable salts thereof, and $C_1$–$C_8$ alkyl esters thereof, wherein $Q_1$ and $Q_4$ are N.

More preferred are compounds of Formula VI

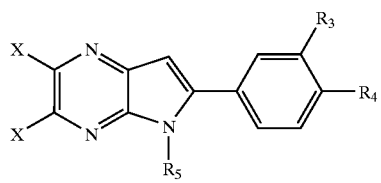

VI wherein X, $R_3$, $R_4$, and $R_5$ are as defined above, and pharmaceutically acceptable salts thereof, and $C_1$–$C_8$ alkyl esters thereof.

Also preferred is a compound of Formula I, and pharmaceutically acceptable salts thereof, and $C_1$–$C_8$ alkyl esters thereof, wherein $Q_2$ and $Q_4$ are N.

More preferred are compounds of Formula VII

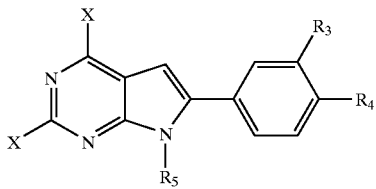

VII wherein X, $R_3$, $R_4$, and $R_5$ are as defined above, and pharmaceutically acceptable salts thereof, and $C_1$–$C_8$ alkyl esters thereof.

Also preferred are compounds of Formula I, and pharmaceutically acceptable salts thereof, and $C_1$–$C_8$ alkyl esters thereof, wherein each of $Q_1$, $Q_2$, $Q_3$, and $Q_4$ is $CH_2$.

More preferred are compounds of Formula VIII

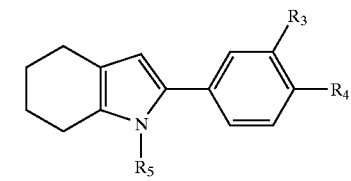

VIII wherein $R_3$, $R_4$, and $R_5$ are as defined above, and pharmaceutically acceptable salts thereof, and $C_1$–$C_8$ alkyl esters thereof.

Also preferred is a compound of Formula I, and pharmaceutically acceptable salts thereof, and $C_1$–$C_8$ alkyl esters thereof, wherein $Q_3$ and $Q_4$ are N.

Also preferred is a compound of Formula I, and pharmaceutically acceptable salts thereof, and $C_1$–$C_8$ alkyl esters thereof, wherein $Q_1$ and $Q_2$ are N.

Also preferred is a compound of Formula I, and pharmaceutically acceptable salts thereof, and $C_1$–$C_8$ alkyl esters thereof, wherein $Q_2$ and $Q_3$ are N.

Also preferred is a compound of Formula I, and pharmaceutically acceptable salts thereof, and $C_1$–$C_8$ alkyl esters thereof, wherein $Q_1$ and $Q_3$ are N.

Also preferred are compounds of Formula IX

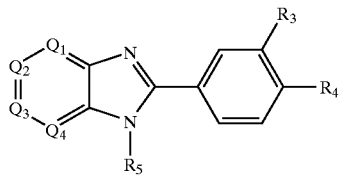

(IX)

wherein $Q_1$, $Q_2$, $Q_3$, $Q_4$, $R_3$, $R_4$, and $R_5$ are as defined above, and pharmaceutically acceptable salts thereof, and $C_1$–$C_8$ alkyl esters thereof.

In another preferred embodiment, the invention provides a compound of Formula (A):

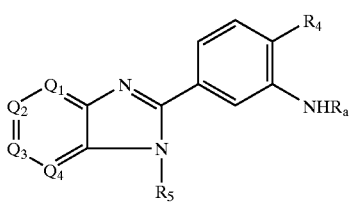

(A)

and pharmaceutically acceptable salts thereof, and $C_1$–$C_8$ alkyl esters thereof,
wherein:
$Q_1$, $Q_2$, $Q_3$, and $Q_4$ are independently selected from CX and N, wherein 1 or 2 of $Q_1$, $Q_2$, $Q_3$, and $Q_4$ are N or each of $Q_1$, $Q_2$, $Q_3$, and $Q_4$ is $CH_2$ and there is a C—C double bond between the carbon atoms bearing $Q_1$ and N, and $Q_4$ and N, respectively, wherein,
X is independently selected from H, halo, hydroxy, $CF_3$, $R_1$, $OR_1$, $CO_2R_1$, $NO_2$, $NH_2$, and $SR_1$, wherein $R_1$ is H or $C_1$–$C_4$ alkyl;
$R_a$ is H, $C_1$–$C_4$ alkyl, $C_3$–$C_8$ cycloalkyl, phenyl, $C_2$–$C_6$ heteroaryl, benzyl, $CH_2$—($C_2$–$C_6$ heterocyclic radical), $C(O)NH_2$, or -M-T, wherein M is sulfonyl, $SO_2NR_b$, $CONR_b$, $CSNR_b$, or $CSR_b$, wherein $R_b$ is H, $C_1$–$C_4$ alkyl, or $C_2$–$C_6$ heterocyclic radical, and T is $C_1$–$C_{18}$ alkyl, phenyl, or $C_2$–$C_6$ heterocyclic radical;
$R_4$ is $C_1$–$C_2$ alkoxy, $C_1$–$C_2$ thioalkoxy, hydroxy, halo, or $C_1$–$C_4$ alkyl;
$R_5$ is H, (phenyl)($C_1$–$C_4$ alkyl)oxycarbonyl, ($C_1$–$C_4$ alkyl) oxycarbonyl, ($C_3$–$C_8$ cycloalkyl)oxycarbonyl, ($C_3$–$C_8$ cycloalkyl), ($C_1$–$C_4$ alkyl)oxycarbonyl, or ($C_6$–$C_{10}$ aryl) oxycarbonyl;
wherein each hydrocarbyl or heterocyclic radical above is optionally substituted with between 1 and 3 substituents independently selected from halo, $C_1$–$C_4$ alkyl, $C_3$–$C_6$ cycloalkyl, $C_1$–$C_4$ alkenyl, $C_1$–$C_4$ alkynyl, phenyl, hydroxyl, amino, (amino)sulfonyl, N-acetyl, O-acetyl, $C_1$–$C_4$ thioalkyl, $C_1$–$C_4$ alkoxy, $COOR_6$, wherein $R_6$ is H or $C_1$–$C_6$ alkyl, $SO_3Na$, $SO_3H$, $SO_2NH_2$, cyano, $CH_2NH_2$, acetyl, di($C_1$–$C_4$ alkyl)amino, and nitro, wherein each substituent alkyl, cycloalkyl, alkenyl, alkynyl, or phenyl is in turn optionally substituted with between 1 and 3 substituents independently selected from halo, $C_1$–$C_2$ alkyl, hydroxyl, amino, and nitro.

Also preferred is a compound of Formula I, and pharmaceutically acceptable salts thereof, and $C_1$–$C_8$ alkyl esters thereof, wherein $R_a$ or $R_b$ is a heterocyclic radical selected from 3-pyridyl, 3-picolinyl, 2-thienyl, 3-thienyl, dansyl, 8-quinoyl, and imidazolyl.

Also preferred is a compound of Formula I, and pharmaceutically acceptable salts thereof, and $C_1$–$C_8$ alkyl esters thereof, wherein $R_a$ or $R_b$ is one of said phenyl, benzyl, alkyl, heterocyclic radical, or cycloalkyl groups substituted with at least one substituent selected from halo, hydroxyl, amino, (amino)sulfonyl, N-acetyl, O-acetyl, $C_1$–$C_4$ thioalkyl, $C_1$–$C_4$ alkoxy, $COOR_6$, $SO_3Na$, $SO_3H$, $SO_2NH_2$, cyano, $CH_2NH_2$, acetyl, di($C_1$–$C_4$ alkyl)amino, trifluoromethyl, and nitro, and wherein W is a covalent bond.

Also preferred is a compound of Formula I, and pharmaceutically acceptable salts thereof, and $C_1$–$C_8$ alkyl esters thereof, wherein said substituent is $CO_2R_6$, N-acetyl, di($C_1$–$C_4$ alkyl)amino, hydroxy, halo, or trifluoromethyl.

Preferred is a compound of Formula I, and pharmaceutically acceptable salts thereof, and $C_1$–$C_8$ alkyl esters thereof, wherein $R_a$ is a phenyl or benzyl having a substituent in the 3- or 4-position, substituents in the 3- and 5-positions, or substituents in the 3- and 4-positions.

Also preferred is a compound of Formula I, and pharmaceutically acceptable salts thereof, and $C_1$–$C_8$ alkyl esters thereof, wherein $R_a$ is $C_1$–$C_4$ alkylsulfonyl or $C_{10}$–$C_{14}$ alkylsulfonyl.

Preferred is a compound of Formula I, and pharmaceutically acceptable salts thereof, and $C_1$–$C_8$ alkyl esters thereof, wherein $R_4$ is methoxy, hydroxy, or thiomethoxy.

Preferred is a compound of Formula I, and pharmaceutically acceptable salts thereof, and $C_1$–$C_8$ alkyl esters thereof, wherein $R_4$ is methoxy.

Preferred is a compound of Formula I, and pharmaceutically acceptable salts thereof, and $C_1$–$C_8$ alkyl esters thereof, wherein $R_5$ is H.

Still more preferred is a compound selected from the group consisting of:
1-(3,5-Dichloro-phenyl)-3-[5-(3H-imidazo[4,5-b]pyridin-2-yl)-2-methoxy-phenyl]-thiourea;
[5-(3H-Imidazo[4,5-b]pyridin-2-yl)-2-methoxy-phenyl]-urea;
5-(3H-Imidazo[4,5-c]pyridin-2-yl)-2-methoxy-phenylamine;
5-(3H-Imidazo[4,5-b]pyridin-2-yl)-2-methoxy-phenylamine (Chemical Example 1);
1-(3,5-Dichloro-phenyl)-3-[5-(3H-imidazo[4,5-c]pyridin-2-yl)-2-methoxy-phenyl]-thiourea;
[5-(3H-Imidazo[4,5-c]pyridin-2-yl)-2-methoxy-phenyl]-urea;
Thiophene-2-sulfonic acid [5-(3H-imidazo[4,5-b]pyridin-2-yl)-2-methoxy-phenyl]-amide (Chemical Example 2);
Thiophene-2-sulfonic acid [5-(3H-imidazo[4,5-c]pyridin-2-yl)-2-methoxy-phenyl]-amide;
2-Methoxy-5-(9H-purin-8-yl)-phenylamine;
1-(3,5-Dichloro-phenyl)-3-[2-methoxy-5-(9H-purin-8-yl)-phenyl]-thiourea;
[2-Methoxy-5-(9H-purin-8-yl)-phenyl]-urea;
Thiophene-2-sulfonic acid [2-methoxy-5-(9H-purin-8-yl)-phenyl]-amide;
5-(7H-Imidazo[4,5-c]pyridazin-6-yl)-2-methoxy-phenylamine;
1-(3,5-Dichloro-phenyl)-3-[5-(7H-imidazo[4,5-c]pyridazin-6-yl)-2-methoxy-phenyl]-thiourea;
[5-(7H-Imidazo[4,5-c]pyridazin-6-yl)-2-methoxy-phenyl]-urea;
Thiophene-2-sulfonic acid [5-(7H-imidazo[4,5-c]pyridazin-6-yl)-2-methoxy-phenyl]-amide;
5-(1H-Imidazo[4,5-d]pyridazin-2-yl)-2-methoxy-phenylamine;
1-(3,5-Dichloro-phenyl)-3-[5-(1H-imidazo[4,5-d]pyridazin-2-yl)-2-methoxy-phenyl]3-thiourea;
[5-(1H-Imidazo[4,5-d]pyridazin-2-yl)-2-methoxy-phenyl]-urea;

Thiophene-2-sulfonic acid [5-(1H-imidazo[4,5-d]pyridazin-2-yl)-2-methoxy-phenyl]-amide;
5-(1H-Imidazo[4,5-b]pyrazin-2-yl)-2-methoxy-phenylamine;
1-(3,5-Dichloro-phenyl)-3-[5-(1H-imidazo[4,5-b]pyrazin-2-yl)-2-methoxy-phenyl]-thiourea;
[5-(1H-Imidazo[4,5-b]pyrazin-2-yl)-2-methoxy-phenyl]-urea; and
Thiophene-2-sulfonic acid [5-(1H-imidazo[4,5-b]pyrazin-2-yl)-2-methoxy-phenyl]-amide.

Also still more preferred is a compound selected from the group consisting of:
Thiophene-2-sulfonic acid [2-methoxy-5-(1H-pyrrolo[2,3-b]pyridin-2-yl)-phenyl]-amide;
[2-Methoxy-5-(1H-pyrrolo[2,3-b]pyridin-2-yl)-phenyl]-pyridin-3-ylmethyl-amine;
[2-Methoxy-5-(1H-pyrrolo[2,3-b]pyridin-2-yl)-phenyl]-(3-trifluoromethyl-phenyl)-amine;
3-{[2-Methoxy-5-(1H-pyrrolo[2,3-b]pyridin-2-yl)-phenylamino]-methyl}-phenol;
1-(3,5-Dichloro-phenyl)-3-[2-methoxy-5-(1H-pyrrolo[2,3-b]pyridin-2-yl)-phenyl]-thiourea;
1-(3,5-Dichloro-phenyl)-3-[2-methoxy-5-(1H-pyrrolo[2,3-c]pyridin-2-yl)-phenyl]-thiourea;
Thiophene-2-sulfonic acid [2-methoxy-5-(1H-pyrrolo[2,3-c]pyridin-2-yl)-phenyl]-amide;
[2-Methoxy-5-(1H-pyrrolo[2,3-c]pyridin-2-yl)-phenyl]-pyridin-3-ylmethyl-amine;
[2-Methoxy-5-(1H-pyrrolo[2,3-c]pyridin-2-yl)-phenyl]-(3-trifluoromethyl-phenyl)-amine;
3-{[2-Methoxy-5-(1H-pyrrolo[2,3-c]pyridin-2-yl)-phenylamino]-methyl}-phenol;
1-(3,5-Dichloro-phenyl)-3-[2-methoxy-5-(1H-pyrrolo[3,2-c]pyridin-2-yl)-phenyl]-thiourea;
Thiophene-2-sulfonic acid [2-methoxy-5-(1H-pyrrolo[3,2-c]pyridin-2-yl)-phenyl]-amide;
[2-Methoxy-5-(1H-pyrrolo[3,2-c]pyridin-2-yl)-phenyl]-pyridin-3-ylmethyl-amine;
[2-Methoxy-5-(1H-pyrrolo[3,2-c]pyridin-2-yl)-phenyl]-(3-trifluoromethyl-phenyl)-amine;
3-{[2-Methoxy-5-(1H-pyrrolo[3,2-c]pyridin-2-yl)-phenylamino]-methyl}-phenol;
1-(3,5-Dichloro-phenyl)-3-[2-methoxy-5-(1H-pyrrolo[3,2-b]pyridin-2-yl)-phenyl]-thiourea;
Thiophene-2-sulfonic acid [2-methoxy-5-(1H-pyrrolo[3,2-b]pyridin-2-yl)-phenyl]-amide;
[2-Methoxy-5-(1H-pyrrolo[3,2-b]pyridin-2-yl)-phenyl]-pyridin-3-ylmethyl-amine;
[2-Methoxy-5-(1H-pyrrolo[3,2-b]pyridin-2-yl)-phenyl]-(3-trifluoromethyl-phenyl)-amine; and
3-{[2-Methoxy-5-(1H-pyrrolo[3,2-b]pyridin-2-yl)-phenylamino]-methyl}-phenol.

Also still more preferred is a compound selected from the group consisting of:
1-(3,5-Dichloro-phenyl)-3-[2-methoxy-5-(5H-pyrrolo[2,3-b]pyrazin-6-yl)-phenyl]-thiourea;
Thiophene-2-sulfonic acid [2-methoxy-5-(5H-pyrrolo[2,3-b]pyrazin-6-yl)-phenyl]-amide;
[2-Methoxy-5-(5H-pyrrolo[2,3-b]pyrazin-6-yl)-phenyl]-pyridin-3-ylmethyl-amine;
[2-Methoxy-5-(5H-pyrrolo[2,3-b]pyrazin-6-yl)-phenyl]-(3-trifluoromethyl-phenyl)-amine;
3-{[2-Methoxy-5-(5H-pyrrolo[2,3-b]pyrazin-6-yl)-phenylamino]-methyl}-phenol;
1-(3,5-Dichloro-phenyl)-3-[2-methoxy-5-(7H-pyrrolo[2,3-c]pyridazin-6-yl)-phenyl]-thiourea;
Thiophene-2-sulfonic acid [2-methoxy-5-(7H-pyrrolo[2,3-c]pyridazin-6-yl)-phenyl]-amide;
[2-Methoxy-5-(7H-pyrrolo[2,3-c]pyridazin-6-yl)-phenyl]-pyridin-3-ylmethyl-amine;
[2-Methoxy-5-(7H-pyrrolo[2,3-c]pyridazin-6-yl)-phenyl]-(3-trifluoromethyl-phenyl)-amine;
3-{[2-Methoxy-5-(7H-pyrrolo[2,3-c]pyridazin-6-yl)-phenylamino]-methyl}-phenol;
1-(3,5-Dichloro-phenyl)-3-[2-methoxy-5-(5H-pyrrolo[3,2-c]pyridazin-6-yl)-phenyl]-thiourea;
Thiophene-2-sulfonic acid [2-methoxy-5-(5H-pyrrolo[3,2-c]pyridazin-6-yl)-phenyl]-amide;
[2-Methoxy-5-(5H-pyrrolo[3,2-c]pyridazin-6-yl)-phenyl]-pyridin-3-ylmethyl-amine;
[2-Methoxy-5-(5H-pyrrolo[3,2-c]pyridazin-6-yl)-phenyl]-(3-trifluoromethyl-phenyl)-amine;
3-{[2-Methoxy-5-(5H-pyrrolo[3,2-c]pyridazin-6-yl)-phenylamino]-methyl}-phenol;
1-(3,5-Dichloro-phenyl)-3-[2-methoxy-5-(1H-pyrrolo[2,3-d]pyridazin-2-yl)-phenyl]-thiourea;
Thiophene-2-sulfonic acid [2-methoxy-5-(1H-pyrrolo[2,3-d]pyridazin-2-yl)-phenyl]-amide;
[2-Methoxy-5-(1H-pyrrolo[2,3-d]pyridazin-2-yl)-phenyl]-pyridin-3-ylmethyl-amine;
[2-Methoxy-5-(1H-pyrrolo[2,3-d]pyridazin-2-yl)-phenyl]-(3-trifluoromethyl-phenyl)-amine;
3-{[2-Methoxy-5-(1H-pyrrolo[2,3-d]pyridazin-2-yl)-phenylamino]-methyl}-phenol;
1-(3,5-Dichloro-phenyl)-3-[2-methoxy-5-(7H-pyrrolo[2,3-d]pyrimidin-6-yl)-phenyl]-thiourea;
Thiophene-2-sulfonic acid [2-methoxy-5-(7H-pyrrolo[2,3-d]pyrimidin-6-yl)-phenyl]-amide;
[2-Methoxy-5-(7H-pyrrolo[2,3-d]pyrimidin-6-yl)-phenyl]-pyridin-3-ylmethyl-amine;
[2-Methoxy-5-(7H-pyrrolo[2,3-d]pyrimidin-6-yl)-phenyl]-(3-trifluoromethyl-phenyl)-amine;
3-{[2-Methoxy-5-(7H-pyrrolo[2,3-d]pyrimidin-6-yl)-phenylamino]-methyl}-phenol;
1-(3,5-Dichloro-phenyl)-3-[2-methoxy-5-(5H-pyrrolo[3,2-d]pyrimidin-6-yl)-phenyl]-thiourea;
Thiophene-2-sulfonic acid [2-methoxy-5-(5H-pyrrolo[3,2-d]pyrimidin-6-yl)-phenyl]-amide;
[2-Methoxy-5-(5H-pyrrolo[3,2-d]pyrimidin-6-yl)-phenyl]-pyridin-3-ylmethyl-amine;
[2-Methoxy-5-(5H-pyrrolo[3,2-d]pyrimidin-6-yl)-phenyl]-(3-trifluoromethyl-phenyl)-amine; and
3-{[2-Methoxy-5-(5H-pyrrolo[3,2-d]pyrimidin-6-yl)-phenylamino]-methyl}-phenol.

Also still more preferred is a compound of Formula I selected from the group consisting of:
1-(3,5-Dichloro-phenyl)-3-[2-methoxy-5-(4,5,6,7-tetrahydro-1H-indol-2-yl)-phenyl]-thiourea;
Thiophene-2-sulfonic acid [2-methoxy-5-(4,5,6,7-tetrahydro-1H-indol-2-yl)-phenyl]-amide;
[2-Methoxy-5-(4,5,6,7-tetrahydro-1H-indol-2-yl)-phenyl]-pyridin-3-ylmethyl-amine;
[2-Methoxy-5-(4,5,6,7-tetrahydro-1H-indol-2-yl)-phenyl]-(3-trifluoromethyl-phenyl)-amine; and
3-{[2-Methoxy-5-(4,5,6,7-tetrahydro-1H-indol-2-yl)-phenylamino]-methyl}-phenol.

The invention also provides pharmaceutical compositions comprising compounds of Formula I, together with a pharmaceutically acceptable carrier, diluent, or excipient. Preferred compositions comprise a compound of Formulas II through IX or (A) with a pharmaceutically acceptable carrier, diluent, or excipient.

The invention also provides methods for treating mammals with diseases relating to the 15-LO cascade. These methods are for treating, preventing, or ameliorating the related condition or disease. These methods include the following.

A method for inhibiting 15-LO, said method comprising administering to a patient in need of 15-lipoxygenase inhibition a pharmaceutically-effective amount of a compound of Formula I, or a pharmaceutically acceptable salt thereof, or $C_1$–$C_8$ alkyl esters thereof.

A method for treating or preventing atherosclerosis, said method comprising administering to a patient at risk or in need of such treatment a therapeutically-effective amount of a compound of Formula I, or a pharmaceutically acceptable salt thereof, or $C_1$–$C_8$ alkyl esters thereof.

A method for inhibiting the chemotaxis of monocytes, said method comprising administering to a patient in need of inhibition of monocytic migration a therapeutically-effective amount of a compound of Formula I, or a pharmaceutically acceptable salt thereof, or $C_1$–$C_8$ alkyl esters thereof.

A method for treating or preventing inflammation, said method comprising administering to patient at risk or in need of such treatment a therapeutically-effective amount of a compound of Formula I, or a pharmaceutically acceptable salt thereof, or $C_1$–$C_8$ alkyl esters thereof.

A method for treating or preventing stroke, said method comprising administering to a patient at risk or in need of such treatment a therapeutically-effective amount of a compound of Formula I, or a pharmaceutically acceptable salt thereof, or $C_1$–$C_8$ alkyl esters thereof.

A method for treating or preventing coronary artery disease, said method comprising administering to a patient at risk or in need of such treatment a therapeutically-effective amount of a compound of Formula I, or a pharmaceutically acceptable salt thereof, or $C_1$–$C_8$ alkyl esters thereof.

A method for treating or preventing asthma, said method comprising administering to patient at risk or in need of such treatment a therapeutically-effective amount of a compound of Formula I, or a pharmaceutically acceptable salt thereof, or $C_1$–$C_8$ alkyl esters thereof.

A method for treating or preventing arthritis, said method comprising administering to patient at risk or in need of such treatment a therapeutically-effective amount of a compound of Formula I, or a pharmaceutically acceptable salt thereof, or $C_1$–$C_8$ alkyl esters thereof.

A method for treating or preventing colorectal cancer, said method comprising administering to a patient at risk or in need of such treatment a therapeutically-effective amount of a compound of Formula I, or a pharmaceutically acceptable salt thereof, or $C_1$–$C_8$ alkyl esters thereof.

A method for treating or preventing psoriasis, said method comprising administering to a patient at risk or in need of such treatment a therapeutically-effective amount of a compound of Formula I, or a pharmaceutically acceptable salt thereof, or $C_1$–$C_8$ alkyl esters thereof.

Other aspects and features of the invention will be apparent from the disclosure, examples, and claims set forth below.

DETAILED DESCRIPTION OF THE INVENTION

The invention provides compounds of Formula I and methods of making and using them. Other features of the invention, and preferred embodiments thereof, will become apparent from the examples and claims below.

A. Terms

Certain terms used herein are defined below and by their usage throughout this disclosure.

Alkyl groups include aliphatic (i.e., hydrocarbon radicals containing hydrogen and carbon atoms) with a free valence. Alkyl groups are understood to include straight chain and branched structures. Preferred alkyl groups have from 1 to 6 carbon atoms. Examples of typical alkyl groups include methyl, ethyl, propyl, isopropyl, butyl, n-butyl, isobutyl, t-butyl, pentyl, isopentyl, 2,3-dimethylpropyl, hexyl, 2,3-dimethyl hexyl, 1,1-dimethylpentyl, heptyl, and octyl. Cycloalkyl groups are $C_3$–$C_8$ cyclic structures, examples of which include cyclopropyl, cyclobutyl, cyclopentyl, cyclohexyl, and cyclooctyl.

Alkyl and cycloalkyl groups can be substituted with 1, 2, 3 or more substituents which are independently selected from halo (fluoro, chloro, bromo, or iodo), hydroxy, amino, alkoxy, alkylamino, dialkylamino, cycloalkyl, aryl, aryloxy, arylalkyloxy, heterocyclic radical, (heterocyclic radical)oxy, (amino)sulfonyl, N-acetyl, O-acetyl, $C_1$–$C_4$ thioalkyl, $C_1$–$C_4$ alkoxy, $COOR_6$, $SO_3Na$, $SO_3H$, $SO_2NH_2$, cyano, $CH_2NH_2$, acetyl, trifluoromethyl, and nitro. Specific examples include COOH, thiomethyl, methoxy, ethoxy, dimethylamino, ethylmethylamino, diethylamino, and chloro. Other examples include fluoromethyl, hydroxyethyl, 2,3-dihydroxyethyl, (2- or 3-furanyl)methyl, cyclopropylmethyl, methylcyclopropyl, benzyloxyethyl, (3-pyridinyl)methyl, (2- or 3-furanyl)methyl, (2-thienyl)ethyl, hydroxypropyl, aminocyclohexyl, 2-dimethylaminobutyl, methoxymethyl, 2-ethoxycyclopentyl, N-pyridinylethyl, diethylaminoethyl and cyclobutylmethyl.

Alkenyl groups are analogous to alkyl groups, but have at least one double-bond (two adjacent $sp^2$ carbon atoms). Depending on the placement of a double-bond and substituents, if any, the geometry of the double-bond may be entgegen (E), zusammen (Z), cis, or trans. Similarly, alkynyl groups have at least one triple-bond (two adjacent sp carbon atoms). Unsaturated alkenyl or alkynyl groups may have one or more double- or triple-bonds, respectively, or a mixture thereof; like alkyl groups, they may be straight chain or branched, and they may be substituted as described above and throughout the disclosure. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl, and 2-methyl-2-propenyl.

The foregoing groups are referred to collectively as "hydrocarbyl" groups. More general forms of substituted hydrocarbyls include hydroxyalkyl, hydroxyalkenyl, hydroxyalkynyl, hydroxycycloalkyl, hydroxyaryl, and corresponding forms for the prefixes amino-, halo- (e.g., fluoro-, chloro-, or bromo-), nitro-, alkyl-, phenyl-, cycloalkyl- and so on, or combinations of substituents. According to Formula I, therefore, substituted alkyls include hydroxyalkyl, aminoalkyl, nitroalkyl, haloalkyl, alkylalkyl (branched alkyls, such as methylpentyl), (cycloalkyl)alkyl, phenylalkyl, alkoxy, alkylaminoalkyl, dialkylaminoalkyl, arylalkyl, aryloxyalkyl, arylalkyloxyalkyl, (heterocyclic radical)alkyl, and (heterocyclic radical)oxyalkyl and so on. Where $R_a$ or $R_b$ are both phenyl, for example, $R_a$ thus includes 3-halo-4-hydroxyphenyl, 3-(fluoro or chloro)-4-nitrophenyl, 3,4-dichlorophenyl, 3,5-dichlorophenyl, 3,5-difluorophenyl, 3-hydroxy-4-nitrophenyl, 4-hydroxy-3-nitrophenyl, 3-chlorophenyl, 4-chlorophenyl, 2-fluorophenyl, 3-fluorophenyl, 4-fluorophenyl, 3,4-difluorophenyl, 2,3-difluorophenyl, 2,4-difluorophenyl, 3-trifluoromethylphenyl, 4-trifluoromethylphenyl, 3-aminophenyl, 4-aminophenyl, 3,5-diethylphenyl, 3-methylphenyl, 4-methylphenyl, 3-nitrophenyl, 4-nitrophenyl, 3-nitro-4-chlorophenyl, 3-cyanophenyl, 4-cyanophenyl, 3-methyleneaminophenyl, 4-methyleneaminophenyl, 3-hydroxyphenyl, 4-hydroxyphenyl, 3,4-dihydroxyphenyl, 4-chloro-3-trifluoromethylphenyl, 3-carbomethoxyphenyl, 4-carbomethoxyphenyl, bis(3,5-trifluoromethyl)phenyl, 4-t-butylphenyl, 4-n-butylphenyl, 4-isopropylphenyl; 3-acetylphenyl, 4-sulfonic acid (e.g., sodium salt), 3-carboxyphenyl, 4-carboxyphenyl, 3-methoxyphenyl, 4-methoxyphenyl, 3,4-dimethoxyphenyl, 4-acetamidophenyl, 3-amino-4-halophenyl, 3-alkoxy-4-halophenyl, 3-halo-4-alkylaminophenyl, 4-(N,N-dimethylamino)phenyl, 3-cycloalkylphenyl, 3(3',5'-dihalophenyl)-4-nitrophenyl, 4-aryloxyphenyl, arylalkyloxyphenyl, heterocyclic radical phenyl, (heterocyclic radical)oxy, 4-sulfamoylphenyl (or 4-aminosulfonylphenyl), 3-(alkylcarbonyloxy)phenyl such as 3-acetylphenyl, and 3-($C_1$–$C_4$ thioalkyl)phenyl.

Similarly, the invention features analogous examples of substituted $R_a$ on a heterocyclic radical. Heterocyclic radicals, which include but are not limited to heteroaryls, include cyclic and bicyclic ring moieties having between 1 and 4 heteroatoms selected independently from O, S, and N, and having from 2 to 11 carbon atoms. The rings may be aromatic or nonaromatic, with $sp^2$ or $sp^3$ carbon atoms. Examples include: furyl, oxazolyl, isoxazolyl, thienyl, thiophenyl, thiazolyl, pyrrolyl, imidazolyl, triazolyl such as 1,3,4-triazolyl, tetrazolyl, thiazolyl, oxazolyl, xanthenyl, pyronyl, pyridyl, pyrimidyl, triazinyl, pyrazinyl, pyridazinyl, indolyl, and pyrazolyl. Further examples of heterocyclic radicals include piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl. Particularly preferred heterocyclic radicals include 2-pyridyl, 3-pyridyl, 4-pyridyl, 3-picolinyl, 2-thienyl, 3-thienyl, 2-furyl, 3-furyl, dansyl, 8-quinoyl, 2-acetamido-4-thiazole, and imidazolyl. These may be substituted with one or more substituents such as halo, $C_1$–$C_4$ alkoxy, $COOR_6$, $SO_3Na$, $SO_3H$, $SO_2NH_2$, cyano, $CH_2NH_2$, acetyl, trifluoromethyl. Examples of substituted heterocyclic radicals include chloropyranyl, methylthienyl, fluoropyridyl, amino-1-,4-benzisoxazinyl, nitroisoquinolinyl, and hydroxyindolyl. Heterocyclic radicals can be bonded through a carbon atom or a heteroatom.

The term "patient" means a mammal such as a human or a domestic animal such as a dog, cat, horse, bovine, porcine, and sheep.

The term "effective amount" means that quantity of a compound of Formula I that inhibits the 15-LO enzyme in a patient to an extent that results in prevention or treatment of an inflammatory condition or otherwise benefits a patient by virtue of having endogenous 15-LO enzymes inhibited.

The term "halo" includes fluoro, chloro, bromo, and iodo.

The term "amino" means $NH_2$.

The terms "alkoxy" and "thioalkoxy" mean an alkyl group bonded through an oxygen atom or a sulfur atom, respectively, wherein alkyl is defined above unless limited in the number of carbons by a prefix to alkoxy or thioalkoxy such as, for example, $C_1$–$C_2$ or $C_1$–$C_4$.

B. Compounds

The invention compounds can be synthesized utilizing standard organic chemistry methodologies. Typical syntheses are shown in Schemes 1 through 13 below, which are categorized according to "Type" for ease of understanding.

Examples of compounds of the invention categorized by "Type" and reaction Scheme(s) used to prepare the compounds are shown below.

Type A (Schemes 3 and 4)
Thiophene-2-sulfonic acid [2-methoxy-5-(1H-pyrrolo[2,3-b]pyridin-2-yl)-phenyl]-amide;
[2-Methoxy-5-(1H-pyrrolo[2,3-b]pyridin-2-yl)-phenyl]-pyridin-3-ylmethyl-amine;
[2-Methoxy-5-(1H-pyrrolo[2,3-b]pyridin-2-yl)-phenyl]-(3-trifluoromethyl-phenyl)-amine;
3-{[2-Methoxy-5-(1H-pyrrolo[2,3-b]pyridin-2-yl)-phenylamino]-methyl}-phenol; and
1-(3,5-Dichloro-phenyl)-3-[2-methoxy-5-(1H-pyrrolo[2,3-b]pyridin-2-yl)-phenyl]-thiourea.

Type B (Scheme 5)
1-(3,5-Dichloro-phenyl)-3-[2-methoxy-5-(1H-pyrrolo[2,3-b]pyridin-2-yl)-phenyl]-thiourea;
Thiophene-2-sulfonic acid [2-methoxy-5-(1H-pyrrolo[2,3-c]pyridin-2-yl)-phenyl]-amide;
[2-Methoxy-5-(1H-pyrrolo[2,3-c]pyridin-2-yl)-phenyl]-pyridin-3-ylmethyl-amine;
[2-Methoxy-5(1H-pyrrolo[2,3-c]pyridin-2-yl)-phenyl]-(3-trifluoromethyl-phenyl)-amine; and
3-{[2-Methoxy-5-(1H-pyrrolo[2,3-c]pyridin-2-yl)-phenylamino]-methyl}-phenol.

Type C (Scheme 6)
1-(3,5-Dichloro-phenyl)-3-[2-methoxy-5-(1H-pyrrolo[3,2-c]pyridin-2-yl)-phenyl]-thiourea;
Thiophene-2-sulfonic acid [2-methoxy-5-(1H-pyrrolo[3,2-c]pyridin-2-yl)-phenyl]-amide;
[2-Methoxy-5-(1H-pyrrolo[3,2-c]pyridin-2-yl)-phenyl]-pyridin-3-ylmethyl-amine;
[2-Methoxy-5-(1H-pyrrolo[3,2-c]pyridin-2-yl)-phenyl]-(3-trifluoromethyl-phenyl)-amine; and
3-{[2-Methoxy-5-(1H-pyrrolo[3,2-c]pyridin-2-yl)-phenylamino]-methyl}-phenol.

Type D (Scheme 7)
1-3,5-Dichloro-phenyl)-3-[2-methoxy-5-(1H-pyrrolo[3,2-b]pyridin-2-yl)-phenyl]-thiourea;
Thiophene-2-sulfonic acid [2-methoxy-5-(1H-pyrrolo[3,2-b]pyridin-2-yl)-phenyl]-amide;
[2-Methoxy-5-(1H-pyrrolo[3,2-b]pyridin-2-yl)-phenyl]-pyridin-3-ylmethyl-amine;
[2-Methoxy-5-(1H-pyrrolo[3,2-b]pyridin-2-yl)-phenyl]-(3-trifluoromethyl-phenyl)-amine; and
3-{[2-Methoxy-5-(1H-pyrrolo[3,2-b]pyridin-2-yl)-phenylamino]-methyl}-phenol.

Type E (Scheme 8)
1-(3,5-Dichloro-phenyl)-3-[2-methoxy-5-(5H-pyrrolo[2,3-b]pyrazinyl)-phenyl]-thiourea;
Thiophene-2-sulfonic acid [2-methoxy-5-(5H-pyrrolo[2,3-b]pyrazin-6-yl)-phenyl]-amide;
[2-Methoxy-5-(5H-pyrrolo[2,3-b]pyrazin-6-yl)-phenyl]-pyridin-3-ylmethyl-amine;
[2-Methoxy-5-(5H-pyrrolo[2,3-b]pyrazin-6-yl)-phenyl]-(3-trifluoromethyl-phenyl)-amine; and
3-{[2-Methoxy-5-(5H-pyrrolo[2,3-b]pyrazin-6-yl)-phenylamino]-methyl}-phenol.

Type F (Schemes 1 and 2)
1-(3,5-Dichloro-phenyl)-3-[2-methoxy-5-(7H-pyrrolo[2,3-c]pyridazin-6-yl)-phenyl]-thiourea;
Thiophene-2-sulfonic acid [2-methoxy-5-(7H-pyrrolo[2,3-c]pyridazin-6-yl)-phenyl]-amide;
[2-Methoxy-5-(7H-pyrrolo[2,3-c]pyridazin-6-yl)-phenyl]-pyridin-3-ylmethyl-amine;
[2-Methoxy-5-(7H-pyrrolo[2,3-c]pyridazin-6-yl)-phenyl]-(3-trifluoromethyl-phenyl)-amine; and
3-{[2-Methoxy-5-(7H-pyrrolo[2,3-c]pyridazin-6-yl)-phenylamino]-methyl}-phenol.

Type G (Schemes 1 and 2)
1-(3,5-Dichloro-phenyl)-3-[2-methoxy-5-(5H-pyrrolo[3,2-c]pyridazin-6-yl)-phenyl]-thiourea;

Thiophene-2-sulfonic acid [2-methoxy-5-(5H-pyrrolo[3,2-c]pyridazin-6-yl)-phenyl]-amide;
[2-Methoxy-5-(5H-pyrrolo[3,2-c]pyridazin-6-yl)-phenyl]-pyridin-3-ylmethyl-amine;
[2-Methoxy-5-(5H-pyrrolo[3,2-c]pyridazin-6-yl)-phenyl]-(3-trifluoromethyl-phenyl)-amine; and
3-{[2-Methoxy-5-(5H-pyrrolo[3,2-c]pyridazin-6-yl)-phenylamino]-methyl}-phenol.
Type H (Schemes 1 and 2)
1-(3,5-Dichloro-phenyl)-3-[2-methoxy-5-(1H-pyrrolo[2,3-d]pyridazin-2-yl)-phenyl]-thiourea;
Thiophene-2-sulfonic acid [2-methoxy-5-(1H-pyrrolo[2,3-d]pyridazin-2-yl)-phenyl]-amide;
[2-Methoxy-5-(1H-pyrrolo[2,3-d]pyridazin-2-yl)-phenyl]-pyridin-3-ylmethyl-amine;
[2-Methoxy-5-(1H-pyrrolo[2,3-d]pyridazin-2-yl)-phenyl]-(3-trifluoromethyl-phenyl)-amine; and
3-{[2-Methoxy-5-(1H-pyrrolo[2,3-d]pyridazin-2-yl)-phenylamino]-methyl}-phenol.
Type I (Scheme 9)
1-(3,5-Dichloro-phenyl)-3-[2-methoxy-5-(7H-pyrrolo[2,3-d]pyrimidin-6-yl)-phenyl]-thiourea;
Thiophene-2-sulfonic acid [2-methoxy-5-(7H-pyrrolo[2,3-d]pyrimidin-6-yl)-phenyl]-amide;
[2-Methoxy-5-(7H-pyrrolo[2,3-d]pyrimidin-6-yl)-phenyl]-pyridin-3-ylmethyl-amine;
[2-Methoxy-5-(7H-pyrrolo[2,3-d]pyrimidin-6-yl)-phenyl]-(3-trifluoromethyl-phenyl)-amine; and
3-{[2-Methoxy-5-(7H-pyrrolo[2,3-d]pyrimidin-6-yl)-phenylamino]-methyl}-phenol.
Type J (Schemes 1 and 2)
1-(3,5-Dichloro-phenyl)-3-[2-methoxy-5-(5H-pyrrolo[3,2-d]pyrimidin-6-yl)-phenyl]-thiourea;
Thiophene-2-sulfonic acid [2-methoxy-5-(5H-pyrrolo[3,2-d]pyrimidin-6-yl)-phenyl]-amide;
[2-Methoxy-5-(5H-pyrrolo[3,2-d]pyrimidin-6-yl)-phenyl]-pyridin-3-ylmethyl-amine;
[2-Methoxy-5-(5H-pyrrolo[3,2-d]pyrimidin-6-yl)-phenyl]-(3-trifluoromethyl-phenyl)-amine; and
3-{[2-Methoxy-5-(5H-pyrrolo[3,2-d]pyrimidin-6-yl)-phenylamino]-methyl}-phenol.
Type K (Schemes 10 and 11)
1-(3,5-Dichloro-phenyl)-3-[2-methoxy-5-(4,5,6,7-tetrahydro-1H-indol-2-yl)-phenyl]-thiourea;
Thiophene-2-sulfonic acid [2-methoxy-5-(4,5,6,7-tetrahydro-1H-indol-2-yl)-phenyl]-amide;
[2-Methoxy-5-(4,5,6,7-tetrahydro-1H-indol-2-yl)-phenyl]-pyridin-3-ylmethyl-amine;
[2-Methoxy-5-(4,5,6,7-tetrahydro-1H-indol-2-yl)-phenyl]-(3-trifluoromethyl-phenyl)-amine; and
3-{[2-Methoxy-5-(4,5,6,7-tetrahydro-1H-indol-2-yl)-phenylamino]-methyl}-phenol.

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms (at least 90%, and preferably 95%, 98% or greater purity).

Pharmaceutically acceptable salts, esters, and amides include carboxylate salts (e.g., $C_1$–$C_8$ alkyl, cycloalkyl, aryl, heteroaryl, or heterocyclic), amino acid addition salts, esters, and amides which are within a reasonable benefit/risk ratio, pharmacologically effective, and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See, for example, S. M. Berge, et al., "Pharmaceutical Salts," *J. Pharm. Sci.*, 1977;66:1–19 which is incorporated herein by reference. Representative pharmaceutically acceptable amides of the invention include those derived from ammonia, primary $C_1$–$C_6$ alkyl amines and secondary di($C_1$–$C_6$ alkyl)amines. Secondary amines include 5- or 6-membered heterocyclic or heteroaromatic ring moieties containing at least one nitrogen atom and optionally between 1 and 2 additional heteroatoms. Preferred amides are derived from ammonia, $C_1$–$C_3$ alkyl primary amines, and di($C_1$–$C_2$ alkyl)amines. Representative pharmaceutically acceptable esters of the invention include $C_1$–$C_6$ alkyl, $C_5$–$C_7$ cycloalkyl, $C_6$–$C_8$ aryl, and $C_6$–$C_8$ aryl ($C_1$–$C_6$)alkyl esters. Preferred esters include methyl esters.

C. Synthesis

The invention compounds can be synthesized according to the following thirteen schemes, or variants thereof.

Compounds of the present invention can be prepared using the general synthetic procedure shown in Scheme 1. The parent heterocycles can be purchased or synthesized by methods known to those skilled in the art (A. R. Katritzky and C. W. Rees, "Comprehensive Heterocyclic Chemistry, The Structures, Reactions, Synthesis, and Uses of Heterocyclic Compounds," Pergamon Press, NY, 1984;4(3.09): 497–529). The free NH of the heterocycle is protected using the benzenesulfonyl group. The heterocycle of formula (1) is treated with benzenesulfonyl chloride and a base such as potassium or sodium hydroxide in a solvent such as methanol or ethanol to give the protected heterocycle of formula (2). The protected heterocycle of formula (2) is then deprotonated using a base such as n-BuLi in a solvent such as THF or diethyl ether, and the resulting organolithium species is then brominated with bromine to give a compound of formula (3). Lithium-halogen exchange with a base such as n-BuLi in a solvent such as THF or diethyl ether, followed by reaction with triisopropyl borate at temperatures ranging from –20° C. to –78° C. converts the compound of formula (3) to the boronic acid of formula (4). Suzuki coupling of the compound of formula (4) with the aryl bromide of formula (5) in the presence of tetrakis(triphenylphosphine)palladium (0) as catalyst and a base such as aqueous potassium carbonate in a solvent such as toluene gives the protected aryl heterocycle of formula (6). Reduction of the nitro group in the compound of formula (6) can be accomplished with Raney nickel and hydrogen gas in a solvent such as THF or DMF to give the amino compound of formula (7). The compound of formula (7) can be deprotected using HBr in glacial acetic acid to give the compound of formula (8). The compound of formula (8) can be reacted with a variety of compounds such as for example, sulfonyl chlorides, isothiocyanates, aryl halides, and acylchlorides to yield a variety of compounds of the present invention such as for example, sulfonamides, thioureas, N-aryl analogs, and reductive amination products.

Alternatively, compounds of the present invention can be prepared as shown in Scheme 2. In Scheme 2, the bromo compound of formula (3) can be treated with hexamethylditin in a solvent such as benzene using a catalyst such as tetrakis(triphenylphosphine)palladium (0) at reflux temperatures to give the trimethyltin compound of formula (9). Stille coupling of the compound of formula (9) with the aryl bromide of formula (5) in the presence of tetrakis (triphenylphosphine) palladium (0) as catalyst in a solvent such as benzene gives the compound of formula (6), which can be converted to compounds of the present invention as described for Scheme 1.

In addition to the general methods of Schemes 1 and 2, which can be applied to the synthesis of all target compounds, there are other methods available for the synthesis of compounds of the present invention containing more specific ring systems. For the preparation of compounds of the present invention containing the 1H-pyrrolo[2,3-b]pyridine ring system, the method of Houlihan W. J., Parrino V. A., Uike Y., *J. Org. Chem.,* 1981;46:4511–4515 can be employed as shown in Scheme 3. In Scheme 3, a key amide of formula (12) is prepared by reacting the acid of formula (10), which is commercially available, with oxalyl chloride in a solvent such as THF with a catalyst such as DMF to give the corresponding acid chloride, which is then coupled with 2-amino-3-methyl pyridine of formula (11) in a solvent such as toluene using a base such as sodium or potassium carbonate at reflux temperatures to give the amide of formula (12). Treatment of the amide of formula (12) with 2 or 3 equivalents of a base such as n-BuLi or IDA in a solvent such as THF or diethyl ether at temperatures ranging from −20° C. to +25° C. gives the aryl heterocycle of formula (13), which can be converted to sulfonamides, thioureas, N-aryl analogs, and reductive amination products according to the procedure described above for Scheme 1 to provide compounds of the present invention containing the 1H-pyrrolo[2,3-b]pyridine ring system.

In addition, compounds of the present invention containing the 1H-pyrrolo[3,2-b]pyridine ring system can be prepared using the method of Houlihan et al., by replacing 2-amino-3-methyl pyridine of formula (11) with 3-amino-2-methyl pyridine of formula (28) to give a compound of formula (30) as shown in Scheme 7. A compound of formula (30) can be converted to sulfonamides, thioureas, N-aryl analogs, and reductive amination products according to the procedures described above for Scheme 1 to also provide compounds of the present invention containing the 1H-pyrrolo[3,2-b]pyridine ring system.

Alternatively, compounds of the present invention containing the 1H-pyrrolo[2,3-b]pyridine ring system can be prepared utilizing the method of Davis M. L., Wakefield B. J., Wardell J. A., *Tetrahedron,* 1992;48:939–952 as shown in Scheme 4. In Scheme 4, deprotonation of 3-methylpyridine of formula (15) with a base such as LDA in a solvent such as THF or diethyl ether at temperatures ranging from −20° C. to 15° C., followed by reaction of the corresponding anion with the commercially available benzonitrile of formula (14) gives an intermediate of formula (16), which on treatment with additional base cyclizes to give a compound of formula (13). The compound of formula (13) can be converted to sulfonamides, thioureas, N-aryl analogs, and reductive amination products according to the procedures described above for Scheme 1 to provide compounds of the present invention containing the 1H-pyrrolo[2,3-b]pyridine ring system.

In addition, compounds of the present invention containing the 1H-pyrrolo[2,3-b]pyrazine ring system can be prepared using the method of Wakefield et al., by replacing 3-methylpyridine of formula (15) with 2-methylpyrazine of formula (31) to give a compound of formula (33) as shown in Scheme 8. A compound of formula (33) can be converted to sulfonamides, thioureas, N-aryl analogs, and reductive amination products according to the procedures described above for Scheme 1 to provide compounds of the present invention containing the 1H-pyrrolo[2,3-b]pyrazine ring system.

In addition, components of the present invention containing the 7H-pyrrolo[2,3-d]pyrimidine ring system can also be prepared using the method of Wakefield et al. by replacing 3-methylpyridine of formula (15) with 5-methylpyrimidine of formula (34) to give a compound of formula (36) as shown in Scheme 9. A compound of formula (36) can be converted to sulfonamides, thioureas, N-aryl analogs, and reductive amination products according to the procedures described above for Scheme 1 to provide compounds of the present invention containing the 7H-pyrrolo[2,3-d] pyrimidine ring system.

For preparation of compounds of the present invention containing the 1H-pyrrolo[2,3-c]pyridine ring system, the method of Fisher M. H., Schwartkopf G., Jr., Hoff D. R., *J. Med. Chem.,* 1972;15:1168–1171 can be employed as shown in Scheme 5. In Scheme 5, condensation of 3-nitropicoline of formula (17) with the commercially available aldehyde of formula (18) in the presence of a base such as piperidine in a solvent such as methanol or ethanol gives the styrylpyridine of formula (19). The styrylpyridine of formula (19) can be reductively cyclized using triethyl phosphite in a solvent such as benzene at reflux temperatures to yield a compound of formula (20). A compound of formula (20) can be converted to sulfonamides, thioureas, N-aryl analogs, and reductive amination products according to the procedures described above for Scheme 1 to provide compounds of the present invention containing the 1H-pyrrolo[2,3-c]pyridine ring system.

For preparation of compounds of the present invention containing the 1H-pyrrolo[3,2-c]pyridine ring system, another method of Fisher et al., Supra., 1972 can be employed as shown in Scheme 6. In Scheme 6, treatment of 4-chloro-3-methyl pyridine of formula (21) with an oxidizing agent such as m-chloroperoxybenzoic acid in a solvent such as dichloromethane or 1,2-dichloroethane at temperatures ranging from −10° C. to 50° C. gives the corresponding N-oxide of formula (22). The N-oxide of formula (22) is condensed with an aldehyde of formula (18) in the same manner as described in Scheme 5 for the conversion of a compound of formula (18) to a compound of formula (19) to give compound of formula (23). The compound of formula (23) is then reacted with hydrazine in a solvent such as methanol or ethanol to give the hydrazino derivative of formula (24). Reaction of the hydrazino derivative of formula (24) with aqueous sodium nitrite in an acid such as dilute (10%) hydrochloric acid at ambient temperatures gives the azido compound of formula (25), which is thermally decomposed in a solvent such as toluene at reflux temperatures to give the cyclized product formula (26). Reduction of the nitro group and deoxygenation of the pyridine-N-oxide in the cyclized product of formula (26) can be accomplished with Raney nickel and hydrogen gas in a solvent such as THF or DMF to give an amino compound of formula (27). An amino compound of formula (27) can be converted to sulfonamides, thioureas, N-aryl analogs, and reductive amination products according to the procedures described above for Scheme 1 to provide compounds of the present invention containing the 1H-pyrrolo[3,2-c]pyridine ring system.

Compounds of the present invention containing the tetrahydroindole ring system can be prepared as shown in Schemes 10 and 11. In Scheme 10, the method of Hippeli C., Zimmer R., Reissig H.-U., *Liebigs Ann. Chem.*, 1990:469–474 was employed. In this method, treatment of the commercially available ketone of formula (36) with a brominating agent such as N-bromosuccinimide in a solvent such as chloroform or carbon tetrachloride gives the bromo compound of formula (37). Treatment of the bromo compound of formula (37) with hydroxylamine in an aqueous methanol or ethanol solution gives the α-bromooxime of formula (38). Treatment of the α-bromooxime of formula (38) with the silyl enol ether of formula (39) and a base such as sodium carbonate in a solvent such as chloroform or dichloromethane at ambient temperatures gives the dihydro-1,2-oxazine of formula (40). Treatment of the dihydro-1,2-oxazine of formula (40) with molybdenum hexacarbonyl in acetonitrile at reflux temperatures results in deoxygenation and ring contraction to yield the tetrahydroindole of formula (41). The tetrahydroindole of formula (41) can be converted to sulfonamides, thioureas, N-aryl analogs, and reductive amination products according to the procedures described above for Scheme 1 to provide compounds of the present invention containing the tetrahydroindole ring system.

Alternatively, compounds of the present invention containing the tetrahydroindole ring system can be prepared according to the method of Chiu P.-K, Sammes M. P., *Tetrahedron*, 1988;44:3531–3538 as shown in Scheme 11. In Scheme 11, the requisite 1,4-diketone of formula (43) can be prepared by a Stork alkylation of the enamine of formula (42) with the bromo compound of formula (37) in a solvent such as dioxane at reflux temperatures. Paal-Knorr cyclization of the 1,4-diketone of formula (43) with liquid ammonia yields the desired compound of formula (41). The compound of formula (41) can be converted to sulfonamides, thioureas, N-aryl analogs, and reductive amination products according to the procedures described above for Scheme 1 to provide compounds of the present invention containing the tetrahydroindole ring system.

Further compounds of the invention with a fused imidazole ring system, such as those of formula (A), can be made according to Scheme 12. Referring to Scheme 12, a diamino compound of formula (B) is condensed with an activated carboxylic acid compound of formula (C), such as an acid halide or an imidazolide, to give the desired imidazo compound of formula (D). This condensation is a two-step process in which an intermediate amide is formed which then dehydrates to give the imidazo compound of formula (D). These two steps can be done in one pot by refluxing with phosphorous oxychloride. The nitro group of the imidazo compound of formula (D) is reduced with an appropriate reagent such as Raney nickel with hydrogen gas or zinc in acetic acid to give the aniline compound of formula (E). The aniline compound of formula (E) can be converted to a compound of formula (A), wherein $Q_1$, $Q_2$, $Q_3$, $Q_4$, $R_4$, $R_5$, and $R_a$ are as defined above for the compound of formula (A), according to procedures known in the arts of organic and medicinal chemistries for the N-substitution of imidazole derivatives and the preparations of sulfonamides, thioureas, N-aryl analogs, reductive amination analogs, and the like described above for Scheme 1.

An alternative to the above method for the preparation of a compound of formula (A) is illustrated in Scheme 13, wherein the imidazole ring is synthesized last Here, an anilino-benzoate of formula (F) is functionalized to incorporate the $R_a$ group to provide an ester of formula (G). The ester of formula (G) is then hydrolyzed, and the resulting corresponding carboxylic acid is activated with a carboxylic acid activating agent such as, for example, N,N'-carbonyldiimidazole (CDI), N,N'-dicyclohexylcarbodiimide (DCC), and water soluble carbodiimides, and reacted with a di-amino compound of formula (B) under dehydrating conditions to give the compound of formula (A) wherein $R_5$ is hydrogen. The compound of formula (A) wherein $R_5$ is hydrogen can be converted to a compound of formula (A) wherein $R_5$ is as defined above for a compound of formula (A) according to procedures known in the arts of organic and medicinal chemistries for the N-substitution of imidazole derivatives.

Examples of a diamino compound of formula (B) include: 2,3-diaminopyridine, 3,4-diaminopyridine, 4,5-diaminopyrimidine, 3,4-diaminopyridazine, 4,5-diaminopyridazine, and 2,3-diaminopyrazine. 2,3-diaminopyridine, 3,4-diaminopyridine, and 4,5-diaminopyrimidine are from Aldrich Chemicals, Milwaukee, Wis., USA. Other diamino reagents are known in the literature. For example, 2,3-diaminopyrazine can be obtained according to Sato Nobuhiro; Mizuno, Hajime. Studies of pyrazines. Part 33. Synthesis of 2,3-diaminopyrazines via [1,2,5]thiadiazolo[3,4-b]pyrazines., *J. Chem. Res., Synop.*, 1997;7:250–251. 4,5-Diaminopyridazine are obtained according to Marcelis, Antonius T. M.; Tondijs, Hanna; Van der Plas, Henk C. Amination of 4-nitro- and 4-cyanopyridazines by liquid ammonia/potassium permanganate. *J. Heterocycl. Chem.*, 1988;25(3):831–833 and 3,4-diaminopyridazines are obtained according to Klinge D. E.; Van der Plas H. C. NMR studies on σ-adducts of heterocyclic systems with nucleophiles. VII. Proton NMR investigations on σ-adduct formation of pyridazine, of pyridazine 1-oxide, and some of its derivatives with ammonia New substitution mechanism. *Recl. Trav. Chim. Pays-Bas*, 1975;94(11):233–236.

Scheme 1

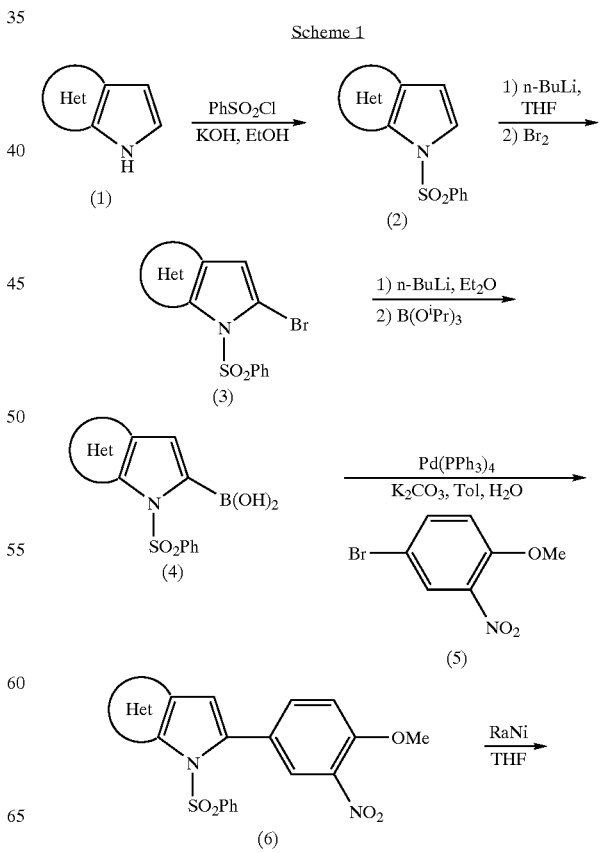

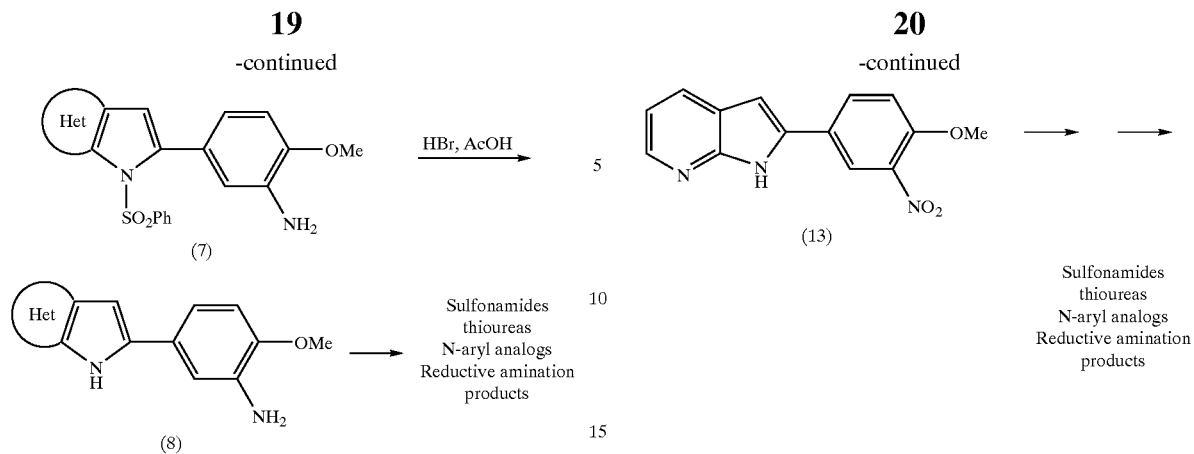
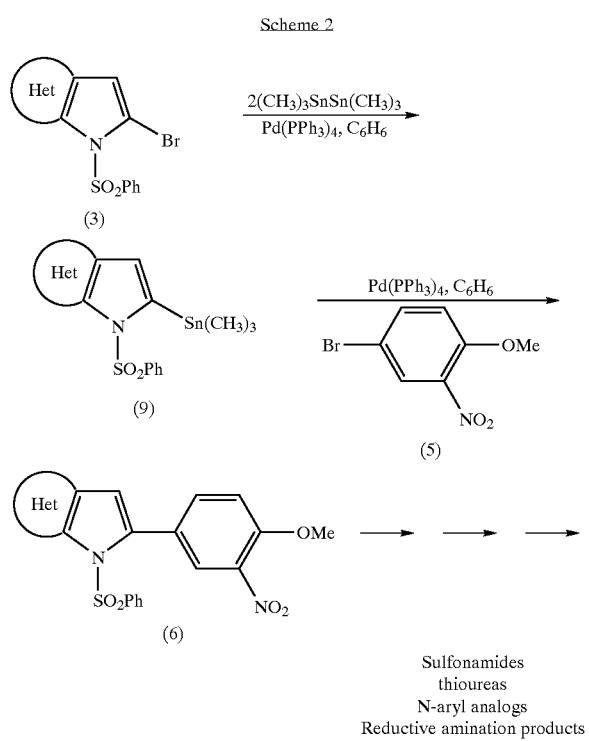
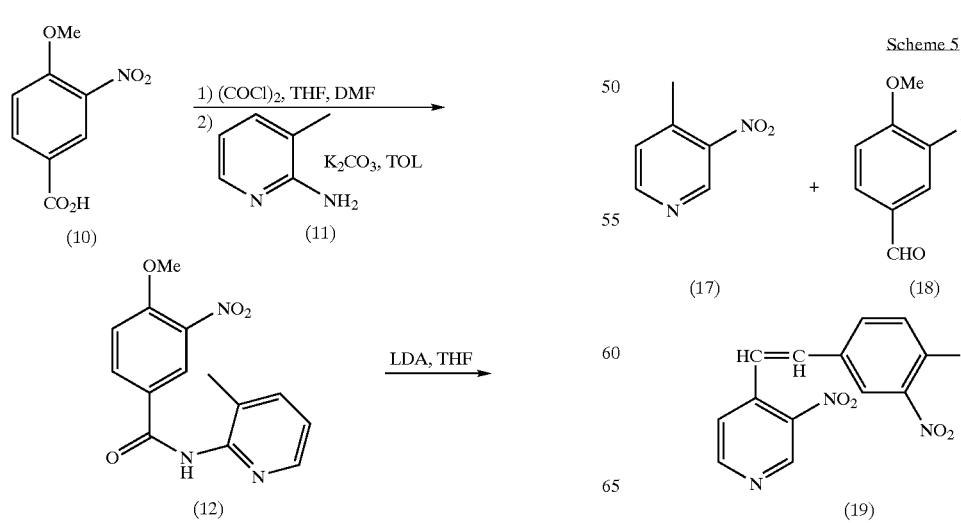

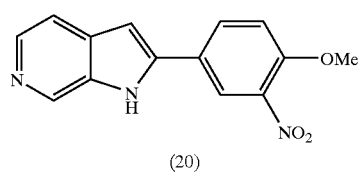
(20)
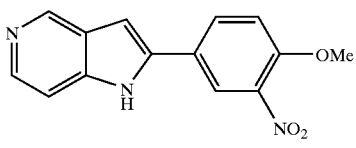
(27)
Sulfonamides
thioureas
N-aryl analogs
Reductive amination
products
Sulfonamides
thioureas
N-aryl analogs
Reductive amination
products
Scheme 6
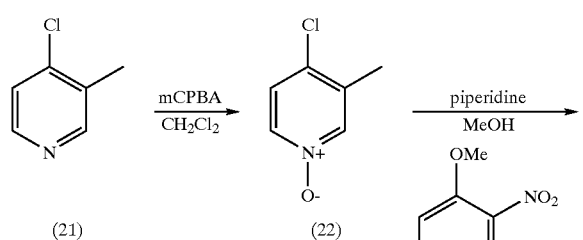
(21)      (22)
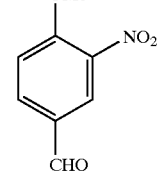
(18)
Scheme 7
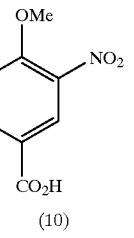
(10)
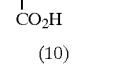
(28)
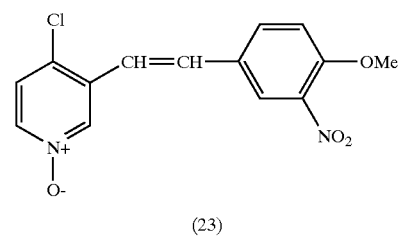
(23)
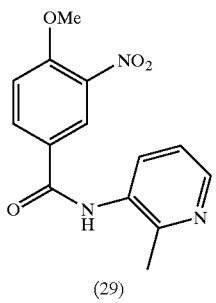
(29)
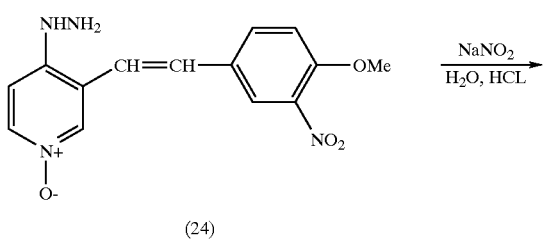
(24)
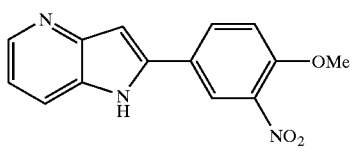
(30)
Sulfonamides
thioureas
N-aryl analogs
Reductive amination
products
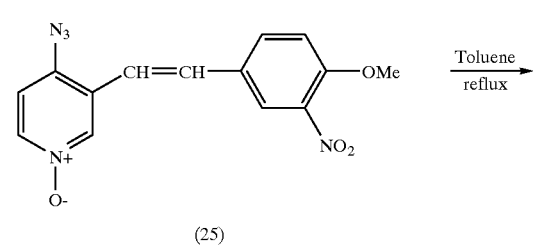
(25)
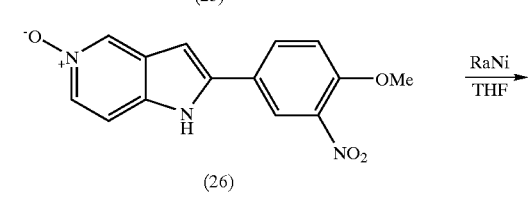
(26)
Scheme 8
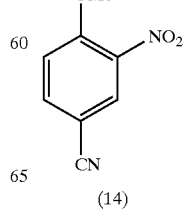
(14)
+
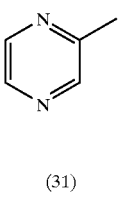
(31)

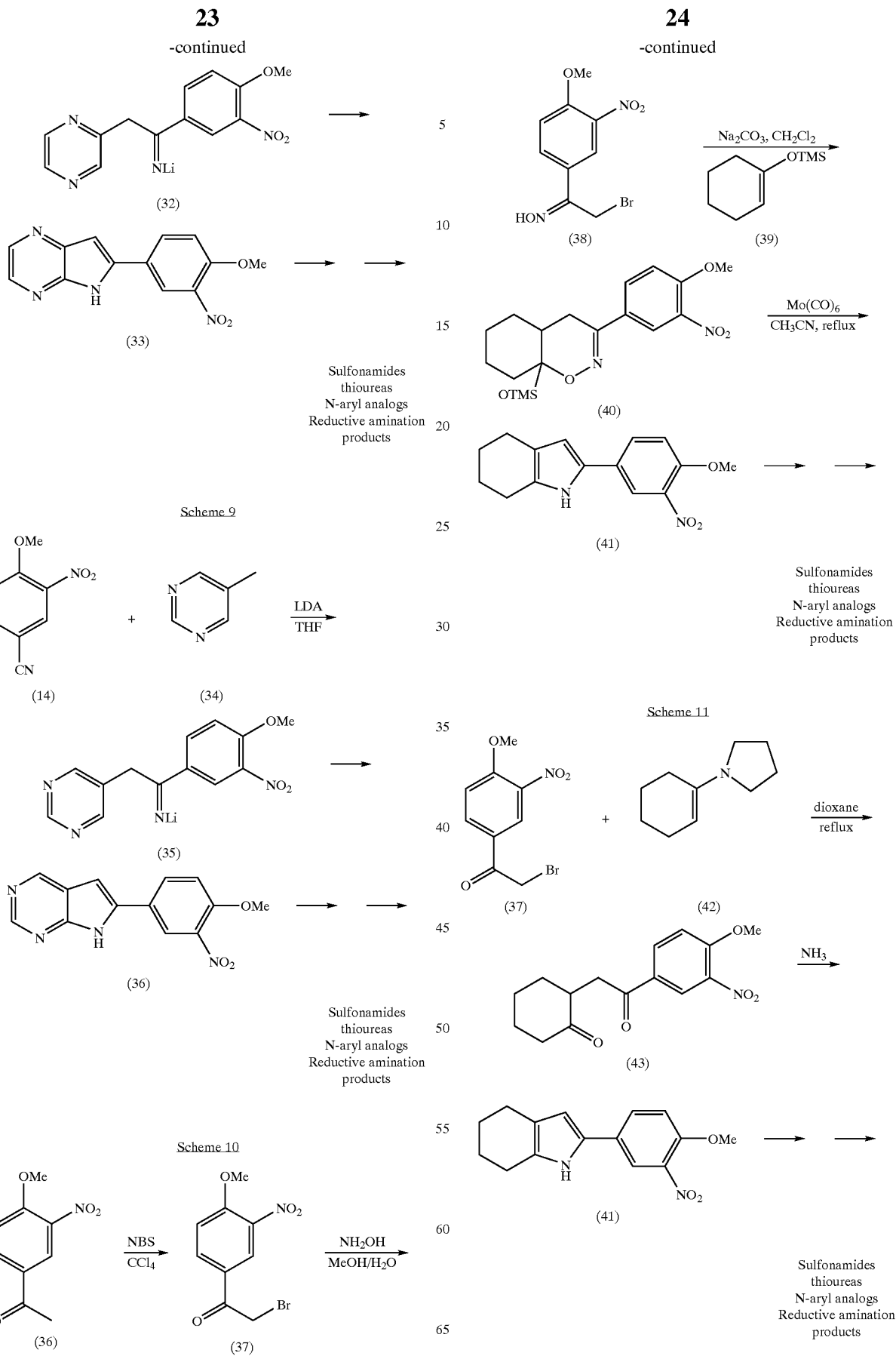

Scheme 12

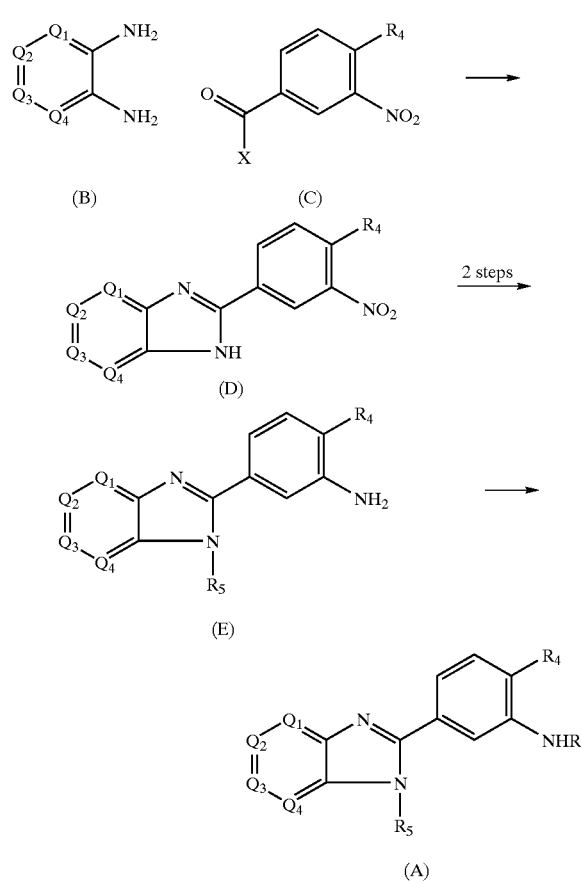

wherein $Q_1$, $Q_2$, $Q_3$, $Q_4$, $R_4$, $R_5$, and $R_a$ are as defined above for formula (A).

Scheme 13

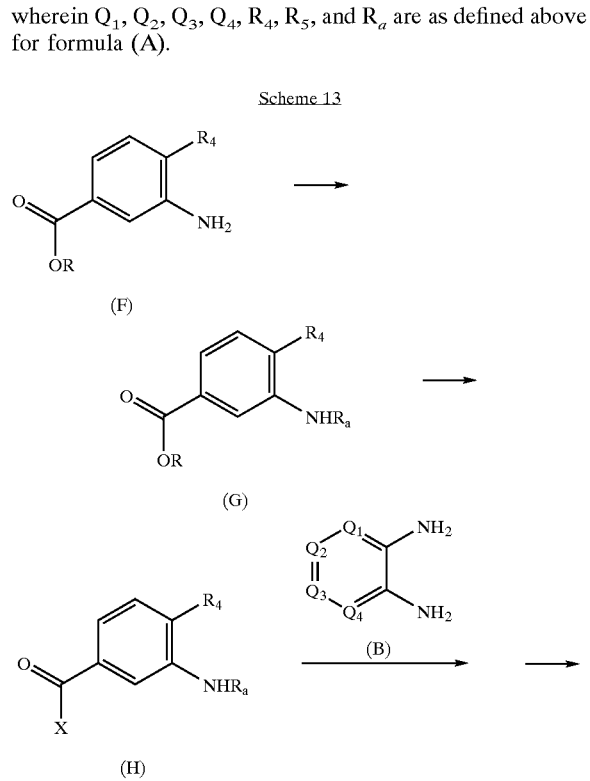

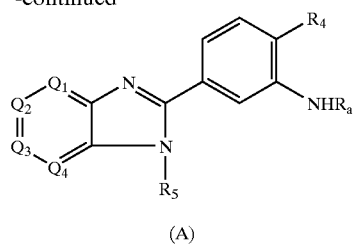

wherein $Q_1$, $Q_2$, $Q_3$, $Q_4$, $R_4$, $R_5$, and $R_a$ are as defined above for formula (A).

The invention also includes disclosed compounds having one or more functional groups (e.g., hydroxyl, amino, or carboxyl) which may be masked by a protecting group so as to avoid unwanted side reactions. Some of these masked or protected compounds are pharmaceutically acceptable; others will be useful as intermediates. Protecting groups such as for example, those for hydroxy, amino, and carboxy groups are well-known to those skilled in the art of synthetic organic chemistry. The use of protecting groups is fully described by Greene and Wuts in "Protecting Groups in Organic Synthesis" (John Wiley & Sons Press, $2^{nd}$ ed.). Examples of suitable protecting groups are provided below.

Hydroxyl Protecting Groups

Hydroxyl protecting groups include: ethers, esters, and protection for 1,2- and 1,3-diols. The ether protecting groups include: methyl ether, substituted methyl ethers including alkyl, cyclic ethers, and cyclic thioethers, substituted ethyl ethers, benzyl ether, substituted benzyl ethers, substituted aryl ethers, and silyl ethers. Silyl ethers can be converted to other functional groups.

Substituted Methyl Ethers

Substituted methyl ethers include: methoxymethyl, methylthiomethyl, t-butylthiomethyl, (phenyldimethylsilyl) methoxymethyl, benzyloxymethyl, p-ethoxybenzyloxymethyl, (4-methoxyphenoxy) methyl, guaiacolmethyl, t-butoxymethyl, 4-pentenyloxymethyl, siloxymethyl, 2-methoxyethoxymethyl, alkyl, benzyl, 2,2,2-trichloroethoxymethyl, bis(2-chloro-ethoxy)methyl, 2-(trimethylsilyl)ethoxymethyl, tetrahydropyranyl, 3-bromotetrahydro-pyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl, and 2,3,3a,4,5,6,7,7a-octahydro-7,8, 8-trimethyl-4,7-ethanobenzofiran-2-yl.

Substituted Ethyl Ethers

Substituted ethyl ethers include: 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, and t-butyl.

Substituted Benzyl Ethers

Substituted benzyl ethers include: p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri-(p-methoxyphenyl) methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris (benzoyloxyphenyl)methyl, 3-(imidazol-1-ylmethyl)bis(4', 4"-dimethoxyphenyl)-methyl, 1,1-bis(4-methoxyphenyl)-1'-pyrenylmethyl, 9-anthryl, 9-(9-phenyl)xanthenyl, 9-(9-phenyl-10-oxo) anthryl, 1,3-benzodithiolan-2-yl, and benzisothiazolyl S,S-dioxido.

Substituted Aryl Ethers

Substituted aryl ethers include p-chlorophenyl, p-methoxyphenyl, and 2,4-dinitrophenyl.

Silyl Ethers

Silyl ethers include: trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxy-phenylsilyl.

Esters

Examples of protective esters of hydroxy groups include: formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, and 2,4,6-trimethylbenzoate (mesitoate).

Carbonates

Carbonate protecting groups of hydroxy groups include: methyl carbonate, 9-fluorenylmethyl carbonate, ethyl carbonate, 2,2,2-trichloroethyl carbonate, 2-(trimethylsilyl) ethyl carbonate, 2-(phenylsulfonyl)ethyl carbonate, 2-(triphenylphosphonio)ethyl carbonate, isobutyl carbonate, vinyl carbonate, alkyl carbonate, p-nitrophenyl carbonate, benzyl carbonate, p-methoxybenzyl carbonate, 3,4dimethoxybenzyl carbonate, o-nitrobenzyl carbonate, p-nitrobenzyl carbonate, S-benzyl thiocarbonate carbonate, 4-ethoxy-1-naphthyl carbonate, and methyl dithiocarbonate.

Assisted Cleavage

Examples of assisted cleavage protecting groups include: 2-iodobenzoate, 4-azido-butyrate, 4-nitro-4-methylpentanoate, o-(dibromomethyl)benzoate, 2-formylbenzene-sulfonate, 2-(methylthiomethoxy)ethyl carbonate, 4-(methylthiomethoxymethyl)benzoate, and 2-(methylthiomethoxymethyl) benzoate. Assisted cleavage protecting groups are groups that contain a second, remote functionality that is unreactive towards the primary functionality masking the group being protected, but which can be converted to a functionality which is reactive towards the primary functionality masking the group being protected such that the deprotective cleavage reaction of the primary functionality is facilitated.

Sulfonates

Protective sulfates include: Methanesulfonate (mesylate), benzylsulfonate, and tosylate.

Miscellaneous Protecting Groups

In addition to the above classes, miscellaneous esters include: 2,6-dichloro-4-methylphenoxyacetate, 2,6-dichloro-4-(1,1,3,3-tetrarmethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl) benzoate, p-P-benzoate, α-naphthoate, nitrate, alkyl N,N,N'N'-tetramethylphosphorodiamidate, N-phenylcarbamate, borate, sulfate, dimethylphosphinothioyl, and 2,4-dinitrophenylsulfenate.

Protection for 1,2- and 1,3-Diols

The protection for 1,2 and 1,3-diols group includes: cyclic acetals and ketals, cyclic ortho esters, and silyl derivatives.

Cyclic Acetals and Ketals

Cyclic acetals and ketals include: methylene, ethylidene, 1-t-butylethylidene, 1-phenylethylidene, (4methoxyphenyl) ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Cyclic ortho esters include: methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino) benzylidene derivative, and 2-oxacyclopentylidene.

Protection for the Carboxyl Group

Esters

Ester protecting groups include: esters, substituted methyl esters including cyclic esters, 2-substituted ethyl esters, benzyl, substituted benzyl esters, silyl esters, activated esters, miscellaneous derivatives, alkyl, and stannyl esters.

Substituted Methyl Esters

Substituted methyl esters include: 9-fluorenylmethyl, methoxymethyl, methylthiomethyl, tetrahydropyranyl, tetrahydrofuranyl, methoxyethoxymethyl, 2-(trimethylsilyl) ethoxy-methyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

2-Substituted ethyl esters include: 2,2,2-trichloroethyl, 2-bromoethyl, 2-chloroalkyl, 2-(trimethylsily)ethyl, 2-methylthioethyl, 1,3-dithianyl-2-methyl, 2-(p-nitrophenylsulfenyl)-ethyl, 2-(p-toluenesulfonyl)ethyl 2-(2'-pyridyl)ethyl, 2-(diphenylphosphino)ethyl, 1-methyl-1-phenylethyl, t-butyl, cyclopentyl, cyclohexyl, 3-buten-1-yl, and 4-(trimethylsilyl)-2-buten-1-yl.

Substituted Benzyl Esters

Substituted benzyl esters include: triphenylmethyl, diphenylmethyl, bis(o-nitrophenyl)methyl, 9-anthrylmethyl, 2-(9,10-dioxo)anthrylmethyl, 5-dibenzo-suberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, and 4-P-benzyl.

Silyl Esters

Silyl esters include: trimethylsilyl, triethylsilyl, t-butyldimethylsilyl, i-propyldimethylsilyl, phenyldimethylsilyl, and di-t-butylmethylsilyl.

Miscellaneous Derivatives

Miscellaneous derivatives include: oxazoles, 2-alkyl-1,3-oxazolines, 4-alkyl-5-oxo-1,3-oxazolidines, 5-alkyl-4-oxo-1,3-dioxolanes, ortho esters, phenyl group, and pentaaminocobalt(III) complex. Aryl esters include phenyl and p-(methylmercapto)-phenyl. Other esters include cinnamyl and α-methyl cinnamyl.

Stannyl Esters

Examples of stannyl esters include: triethylstannyl and tri-n-butylstannyl.

Amides and Hydrazides

Amides include: N,N-dimethyl, pyrrolidinyl, piperidinyl, 5,6-dihydrophenanthridinyl, o-nitroanilides, N-7-nitroindolyl, N-8-nitro-1,2,3,4-tetrahydroquinolyl, and p-P-benzenesulfonamides. Hydrazides include: N-phenyl, N,N'-diisopropyl and other dialkyl hydrazides.

Protection for the Amino Group
Carbamates

Carbamates include: carbamates, substituted ethyl including cyclic substituted ethyl, assisted cleavage, photolytic cleavage, urea-type derivatives, and miscellaneous carbamates.

Carbamates

Carbamates include: methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydro-thioxanthyl)]methyl, and 4-methoxyphenacyl.

Substituted Ethyl

Substituted ethyl protective groups include: 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2,-trichloroethyl, 1-methyl-1-(4biphenylyl)ethyl, 1-(3,5-di-t-butylphenyl)-1-methylethyl, 2-(2'- and 4'-pyridyl)ethyl, 2-(N,N-icyclohexylcarboxamido)-ethyl, t-butyl, and 1-adamantyl.

Miscellaneous groups include: vinyl, alkyl, 1-isopropylalkyl, connamyl, 4-nitrocinnamyl, quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4methylsulfinylbenzyl, 9-anthrylmethyl, and diphenylmethyl.

Assisted Cleavage

Protection via assisted cleavage includes: 2-methylthioethyl, 2-methylsulfonylethyl, 2-(p-toluenesulfonyl)ethyl, [2-(1,3-dithianyl)]methyl, 4-methylthiophenyl, 2,4-dimethyl-thiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolyl-methyl, and 2-(trifluoromethyl)-6-chromonylmethyl. The above definition of assisted cleavage protecting groups is hereby incorporated by reference.

Photolytic Cleavage

Photolytic cleavage methods use groups such as: m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include: phenothiazinyl-(10)-carbonyl derivative, N'-p-toluenesulfonylaminocarbonyl, and N'-phenylaminothiocarbonyl.

Miscellaneous Carbamates

In addition to the above, miscellaneous carbamates include: t-amyl, S-benzyl thiocarbamate, p-cyanobenzyl, cyclobutyl, cyclohexyl, cyclopentyl, cyclopropylmethyl, p-decyloxy-benzyl, diisopropylmethyl, 2,2-dimethoxycarbonylvinyl, o-(N,N-dimethyl-carboxamido)-benzyl, 1,1-dimethyl-3(N,N-dimethylcarboxamido)propyl, 1,1-dimethyl-propynyl, di(2-pyridyl)methyl, 2-furanylmethyl, 2-iodoethyl, isobornyl, isobutyl, isonicotinyl, p(p'-methoxyphenylazo)benzyl, 1-methylcyclobutyl, 1-methylcyclohexyl, 1-methyl-1-cyclopropylmethyl, 1-methyl-(3,5-dimethoxyphenyl)ethyl, 1-methyl-1(p-henylazophenyl)-ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Amides

Amides

Amides include: N-formyl, N-acetyl, N-chloroacetyl, N-trichloroacetyl, N-trifluoroacetyl, N-phenylacetyl, N-3-phenylpropionyl, N-picolinoyl, N-3-pyridyl-carboxamide, N-benzoylphenylalanyl derivative, N-benzoyl, and N-p-phenylbenzoyl.

Assisted Cleavage

Assisted cleavage groups include: N-o-nitrophenylacetyl, N-o-nitrophenoxyacetyl, N-acetoacetyl, (N'-dithiobenzyloxycarbonylamino)acetyl, N-3-(p-hydroxphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one. The above definition of assisted cleavage protecting groups is hereby incorporated by reference.

Cyclic Imide Derivatives

Cyclic imide derivatives include: N-phthalimide, N-dithiasuccinoyl, N-2,3-diphenyl-maleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special —NH Protective Groups

Protective groups for —NH include: N-alkyl and N-aryl amines, imine derivatives, enamine derivatives, and N-heteroatom derivatives (such as N-metal, N—N, N—P, N—Si, and N—S), N-sulfenyl, and N-sulfonyl.

N-Alkyl and N-Aryl Amines

N-alkyl and N-aryl amines include: N-methyl, N-alkyl, N-[2-(trimethylsilyl)ethoxyl]-methyl, N-3-acetoxypropyl, N-(1-isopropyl4-nitro-2-oxo-3-pyrrolin-3-yl), quaternary ammonium salts, N-benzyl, N-di(4methoxyphenyl)methyl, N-5-dibenzosuberyl, N-triphenylmethyl, N-(4methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

Imine derivatives include: N-1,1-dimethylthiomethylene, N-benzylidene, N-p-methoxybenzylidene, N-diphenylmethylene, N-[(2-pyridyl)mesityl]methylene, N-(N',N',-dimethylaminomethylene), N,N'-isopropylidene, N-p-nitrobenzylidene, N-salicylidene, N-5-chlorosalicylidene, N-(5-chloro-2-hydroxyphenyl)-phenylmethylene, and N-cyclohexylidene.

Enamine Derivative

An example of an enamine derivative is N-(5,5-dimethyl-3-oxo-1-cyclohexenyl).

N-Hetero Atom Derivatives

N-metal derivatives include: N-borane derivatives, N-diphenylborinic acid derivative, N-[phenyl(pentacarbonylchromium- or -tungsten)]carbenyl, and N-copper or N-zinc chelate. Examples of N—N derivatives include: N-nitro, N-nitroso, and N-oxide. Examples of N—P derivatives include: N-diphenylphosphinyl, N-dimethylthiophosphinyl, N-diphenylthiophosphinyl, N-dialkyl phosphoryl, N-dibenzyl phosphoryl, and N-diphenyl phosphoryl. Examples of N-sulfenyl derivatives include: N-benzenesulfenyl, N-o-nitrobenzenesulfenyl, N-2,4-dinitrobenzenesulfenyl, N-pentachlorobenzenesulfenyl, N-2-nitro-4-methoxy-benzenesulfenyl, N-triphenylmethylsulfenyl, and N-3-nitropyridinesulfenyl. N-sulfonyl derivatives include: N-p-toluenesulfonyl, N-benzenesulfonyl, N-2, 3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5, 6-tetramethyl-4-methoxybenzene-sulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilylethanesulfonyl, N-9-anthracenesulfonyl, N-4-(4',8'-dimethoxynaphthyl-methyl)-benzenesulfonyl, N-benzylsulfonyl, N-trifluoromethylsulfonyl, and N-phenacyl-sulfonyl.

Disclosed compounds which are masked or protected may be prodrugs, compounds metabolized or otherwise transformed in vivo to yield a disclosed compound, e.g., transiently during metabolism. This transformation may be a hydrolysis or oxidation which results from contact with a bodily fluid such as blood, or the action of acids, or liver, gastrointestinal, or other enzymes.

The invention is further described in the working examples described below. The examples are provided for illustration only, and are not to be construed as limiting the invention in any respect.

D. EXAMPLES

Examples of the preparation of compounds of the present invention and of assays useful in characterizing the biological effects of said compounds are described below.

Chemical Example 1

Synthesis of 5-(3H-imidazo[4,5-b]pyridin-2-yl)-2-methoxy-phenylamine

Step (a): Synthesis of 5-(3H-imidazo[4,5-b]pyridin-2-yl)-2-methoxy-nitrobenzene 2,3-Diaminopyridine (10 g, 91.6 mmol) and 18.07 g of 4-methoxy-3-nitro benzoic acid were mixed together, and the mixture was added in portions to 200 mL of phosphorous oxychloride at. room temperature. The resulting mixture was heated to reflux for 4 hours, and then cooled to room temperature and allowed to stir overnight. The reaction was rotary evaporated in vacuo, and the residue was carefully quenched with saturated sodium bicarbonate solution, filtered, and dried on the vacuum filter overnight to give a brown solid. The solid was washed with several fractions of ethyl acetate to yield 21.36 g of 5-(3H-imidazo[4,5-b]pyridin-2-yl)-2-methoxy-nitrobenzene as a dark brown solid that was used without further purification. $^1$H-NMR (DMSO-$d_6$); δ 8.71 (d, 1H), 8.48 (dd, 1H), 8.31 (dd, 1H), 7.99 (d, 1H), 7.58 (d, 1H), 7.23 (dd, 1H), 4.00 (s, 3H) ppm.

Step (b): Synthesis of 5-(3H-imidazo[4,5-b]pyridin-2-yl)-2-methoxy-phenylamine 5-(3H-Imidazo[4,5-b]pyridin-2-yl)-2-methoxy-nitrobenzene (7.0 g, 26 mmol) was dissolved in 200 mL acetic acid, and zinc powder (35 g, 535 mmol) was added in portions. The zinc was added at such a rate as to keep the temperature of the reaction mixture under 40° C. After complete addition, the reaction mixture was stirred for 3 hours and filtered to give solid. The solids wee washed with water and acetic acid. The filtrate was rotary evaporated in vacuo, and the residue was partitioned between 1 M NaOH and chloroform. The aqueous layer was extracted several times with chloroform, and the combined organic layers were dried over magnesium sulfate, filtered, and rotary evaporated to give 0.71 g of 5-(3H-imidazo[4,5-b]pyridin-2-yl)-2-methoxy-phenylamine as a tan solid. $^1$H-NMR (CDCl$_3$): δ 8.06 (dd, 1H), 7.66 (dd, 1H), 7.41 (s, 1H), 7.35 (dd, 1H), 6.91 (dd, 1H), 6.64 (d, 1H), 3.67 (s, 3H) ppm. Anal. ($C_{13}H_{12}N_4O_1$) C,H,N values were within 0.4% of the theoretical values.

Chemical Example 2

Synthesis of Thiophene-2-sulfonic acid [5-(3H-imidazo[4,5-b]pyridin-2-yl)-2-methoxy-phenyl]-amide 5-(3H-Imidazo[4,5-b]pyridin-2-yl)-2-methoxy-phenylamine (0.5 g, 2.1 mmol prepared as described above in Chemical Example 1) was dissolved in 15 mL pyridine at room temperature. Solid thiophene 2-sulfonyl chloride (0.38 g, 2.1 mmol) was added and the resulting blood red solution was stirred overnight The reaction mixture was poured into 250 mL water, stirred for 30 minutes, and filtered to give a pink solid. The solid was recrystallized from ethyl acetate after treatment with decolorizing charcoal to give 0.16 g of thiophene-2-sulfonic acid [5-(3H-imidazo[4,5-b]pyridin-2-yl)-2-methoxy-phenyl]-amide as an off-white solid; mp 252–254° C. $^1$H-NMR (DMSO-$d_6$): δ 13.26 (d, 1H), 9.85 (bs, 1H), 8.27 (m, 2H), 8.02 (m, 2H), 7.87 (d, 1H), 7.43 (d, 1H), 7.16 (m, 3H), 3.59 (s, 3H) ppm. Anal. ($C_{17}H_{14}N_4O_3S_2$) C,H,N values were within 0.4% of theoretical values.

Biological Example 1

Rabbit Reticulocyte 15-LO Assay (h15LO)

The h15LO assay measures inhibition of 15-LO catalyzed oxidation of linoleic acid to the hydroperoxy fatty acid 13-(S)HPODE, a conjugated diene. In the h15LO assay, a test compound is incubated with 15-LO enzyme in the presence of the linoleic acid substrate. For example, 2 units (U) of rabbit reticulocyte 15-LO and 174 μM linoleic acid are incubated with a known amount of a test compound for 15 minutes at 4° C. The total reaction volume is 100 μL in phosphate buffered saline (PBS) containing 0.2% sodium cholate. The reaction is stopped with 100 μL of mobile phase and 10 μL of triethyl phosphite. 13-(S)HPODE is reduced with triethyl phosphite to the more stable 13-hydroxyoctadecadienoate (13-HODE), which prevents artificial, nonenzymatic lipidperoxidation and product breakdown in the sample. 13-HPODE is quantitated by comparing peak areas of individual samples with those from a standard curve generated using authentic 13-HODE. The test reaction is compared to a control reaction, which is identical to the test reaction except no test compound is present. Percent inhibition is calculated as the amount of 13-HODE produced in the test reaction divided by the amount of 13-HODE produced in the control reaction, expressed as a percent.

15-LO is obtained from phenylhydrazine-treated rabbits and purified according to the method of Rapoport (Rapoport et al., *European Journal of Biochemistry*, 1979;96:545–561).

Biological Example 2

Monocyte Recruitment

The recruitment or chemotaxis of monocytes is assayed by methods well-known to those skilled in the art. In particular, the method set forth in *J. Clin. Invest.*, 1988;82:1853–1863, which is hereby incorporated by reference, can be used.

Biological Example 3

Collagen-Induced Arthritis in Mice

Type II collagen-induced arthritis (CIA) in mice is an experimental model of arthritis that has a number of pathologic, immunologic, and genetic features in common with rheumatoid arthritis. Type II collagen (CII) is a major component of joint cartilage. The disease CIA is induced by immunization of DBA/1 mice with 100 μg of type II collagen delivered intradermally in Freund's complete adjuvant. Disease susceptibility in this model is regulated by the Class II MHC gene locus, which is analogous to the known association of rheumatoid arthritis with the HLA-DR4 gene locus.

A progressive and inflammatory arthritis develops in the majority of the immunized mice, characterized by paw width increases of up to 100%. A test compound is administered to mice in a range of amounts, such as 20, 60, 100, and 200 mg of test compound per kilogram of body weight per day. The duration of the test can be several weeks to a few months, such as 40, 60, or 80 days. A clinical scoring index is used to assess disease progression independently in each paw from Stage 1, erythema and edema (score=1), to Stage 2, joint distortion (score=2), to Stage 3, joint ankylosis (score=3). The disease CIA is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type II collagen, and exhibit a marked cellular response to CII.

Biological Example 4

SCW-Induced Monoarticular Arthritis

Arthritis is induced as described by Schwab et al., *Infection and Immunity*, 1991;59:4436–4442, which is hereby incorporated by reference, with minor modifications. Rats receive 6 μg of sonicated streptococcal cell wall (SCW) particles (in 10 μL Dulbecco's PBS [DPBS]) by an intraarticular injection into the right tibiotalar joint on Day 0. On Day 21, the DTH is initiated with 100 μg of SCW (250 μL) administered IV. For oral compound studies, compounds are suspended in vehicle (0.5% hydroxypropyl-methylcellulose/0.2% Tween 80), sonicated, and administered twice daily (10 mL/kg volume) beginning 1 hour prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on Day 21, and comparing them with volumes at subsequent time points such as Day 22, 23, 24, and 25. Paw volume is determined by mercury plethysmography.

Biological Example 5

Murine Ovalbumin-Induced Eosinophilia

The murine ovalbumin-induced eosinophilia assay measures the increase of eosinophil cells in lungs and upper airways in animals administered a compound of the present invention versus control animals administered only vehicle. In this assay, female C57BL/6 mice are obtained from the Jackson Laboratory (Bar Harbor, Me.). All animals are given food and water ad libitum. Mice are sensitized with a single IP injection of ovalbumin (OVA) (Grade V, Sigma Chemical Company, St Louis, Mo.) adsorbed to aluminum potassium sulfate (alum), (10 μg OVA+9 mg alum in 200 μL saline), or vehicle control (9 mg alum in 200 μL saline) on Day 0. On Day 14, the mice are challenged with a 12-minute inhalation of an aerosol consisting of 1.5% OVA (weight/volume) in saline produced by a nebulizer (small particle generator, model SPAG-2; ICN Pharmaceuticals, Costa Mesa, Calif.). Groups of eight mice are dosed with oral vehicle (0.5% hydroxypropylmethylcellulose/0.25% polyoxethylene-sorbitan monooleate [TWEEN-80]), or a test compound at 10, 30, or 100 mg/kg in oral vehicle, 200 μL per mouse PO. Dosing is performed once per day starting on Day 7 or 13, and extending through Day 16.

For determination of pulmonary eosinophilia, 3 days after the first OVA aerosol challenge (Day 17), the mice are anesthetized with an IP injection of anesthetic (Ketamine/Acepromazine/Xylazine), and the tracheae is exposed and cannulated. The lungs and upper airways are lavaged twice with 0.5 mL of cold PBS. A portion (200 μL) of the bronchoalveolar lavage (BAL) fluid is enumerated using a Coulter counter Model ZB1 (Coulter Electronics, Hialeah, Fla.). The remaining BAL fluid is then centrifuged at 300×g for 5 minutes, and the cells are resuspended in 1 mL of Hank's Balanced salts (HBSS) (Gibco BRL) containing 0.5% fetal calf serum (HyClone) and 10 mM N-2-hydroxyethylpiperazine-N'-2-ethanesulfonic acid (HEPES) (Gibco BRL). The cell suspension is centrifuged in a cytospin (Shandon Southern Insments, Sewickley, Pa.) and stained by Diff Quick (American Scientific Products, McGraw Park, Ill.) to differentiate BAL leukocytes into neutrophil, eosinophil, monocyte, or lymphocyte subsets. The number of eosinophils in the BAL fluid is determined by multiplying the percentage of eosinophils by the total cell count.

Biological Example 6

Human Lysate 15-LO Assay (HUM15LO)

The HUM15LO assay measures inhibition of 15-LO catalyzed oxidation of linoleic acid to the hydroperoxy fatty acid 13-(S)HPODE, a conjugated diene. In the HUM15LO assay, a test compound was incubated with 15-LO enzyme in the presence of the linoleic acid substrate. For example, a known amount of a compound of the present invention and 100 μL of human 15-LO and 174 μM of linoleic acid in PBS containing 0.2% sodium cholate were incubated for 15 minutes at 4° C. The test reaction was stopped with 100 μL of mobile phase and 10 μL of triethyl phosphite. 13-(S)HPODE was reduced with triethyl phosphite to the more stable 13-hydroxyoctadecadienoate (13-HODE), which prevents artificial, nonenzymatic lipidperoxidation and product breakdown in the sample. 13-HPODE was quantitated by comparing peak areas of individual samples with those from a standard curve generated using authentic 13-HODE. The test reaction was compared to a control reaction, which is identical to the test reaction except a test compound is not present. Percent inhibition was calculated as the amount of 13-HODE produced in the test reaction divided by the amount of 13-HODE produced in the control reaction, expressed as a percent.

Human 15-LO was generated in a recombinant 15-lipoxygenase bacculovirus expression system, using Gibco/BRL/Life Technologies' Bac-to-Bac expression reagents; T4 DNA ligase, Kanamycin, Gentamicin, tetracycline, penicillin, streptomycin, Bluo-gal, IPTC; DH10Bac competent cells, SOC, LB medium, Sf-900 II SFM media, Sf9 insect cells, Cell Fectin, and EcoRI, BamHI, and KpnI restriction enzymes.

Human Lysate Data for Representative Compounds 5-(3H-Imidazo[4,5-b]pyridin-2-yl)-2-methoxy-phenylamine (Chemical Example 1): 39% inhibition at 10 μM; and Thiophene-2-sulfonic acid [5-(3H-Imidazo[4,5-b]pyridin-2-yl)-2-methoxy-phenyl]-amide (Chemical Example 2): $IC_{50}$=10 μM.

E. Uses

The disclosed compounds of Formula I will be formulated by standard methods into pharmaceutical compositions that are useful as prophylactic or therapeutic treatments for diseases modulated by the 15-LO cascade. The compositions will be administered to mammals for treating and preventing inflammation and atherosclerosis.

1. Dosages

Those skilled in the art will be able to determine, according to known methods, the appropriate dosage for a patient, taking into account factors such as age, weight, general health, the type of pain requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbents, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

FORMULATION EXAMPLE 1
Tablet Formulation:

| Ingredient | Amount (mg) |
| --- | --- |
| The compound of Chemical Example 1 | 25 |
| Lactose | 50 |
| Cornstarch (for mix) | 10 |
| Cornstarch (paste) | 10 |
| Magnesium stearate (1%) | 5 |
| Total | 100 |

The compound of Chemical Example 1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of diseases responsive to the inhibition of the enzyme 15-lipoxygenase.

Formulation Example 2

Coated Tablets

The tablets of Formulation Example 1 are coated in a customary manner with a coating of sucrose, potato starch, talc, tragacanth, and colorant.

Formulation Example 3

Injection Vials

The pH of a solution of 500 g of the compound of Chemical Example 2 and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the compound of Chemical Example 2.

Formulation Example 4

Suppositories

A mixture of 25 g of the compound of Chemical Example 1, 100 g of soya lecithin, and 1400 g of cocoa butter is fused, poured into molds, and allowed to cool. Each suppository contains 25 mg of the compound of Chemical Example 1.

Formulation Example 5

Solution

A solution is prepared from 1 g of the compound of Chemical Example 2, 9.38 g of $NaH_2PO_4.12H_2O$, 28.48 g of $Na_2HPO_4.12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the compound of Chemical Example 2.

Formulation Example 6

Ointment 500 mg of the compound of Chemical Example 1 is mixed with 99.5 g of petroleum jelly under aseptic conditions. A 5 g portion of the ointment contains 25 mg of the compound of Chemical Example 1.

Formulation Example 7

Capsules

Two kilograms of the compound of Chemical Example 2 are filled into hard gelatin capsules in a customary manner such that each capsule contains 25 mg of the invention compound.

Formulation Example 8

Ampoules

A solution of 2.5 kg of the compound of Chemical Example 1 is dissolved in 60 L of double-distilled water. The solution is sterile filtered, and the filtrate is filled into ampoules. The ampoules are lyophilized under sterile conditions and aseptically sealed. Each ampoule contains 25 mg of the compound of Chemical Example 1.

From the above disclosure and examples, and from the claims below, the essential features of the invention are readily apparent. The scope of the invention also encompasses various modifications and adaptations within the knowledge of addition or removal of a protecting group, or the formation of an ester, pharmaceutical salt, hydrate, acid, or amide of a disclosed compound. Publications cited herein are hereby incorporated by reference in their entirety.

Having described the present invention above, various embodiments of the invention are hereby claimed as follows.

What is claimed is:

1. A compound of Formula I:

wherein:

$Q_1$, $Q_2$, $Q_3$, and $Q_4$ are independently selected from CX and N, wherein 1 of $Q_1$, $Q_2$, $Q_3$, and $Q_4$ is N and X is independently selected from H, halo, hydroxy, $CF_3$, $R_1$, $OR_1$, $CO_2R_1$, $NO_2$, $NH_2$, and $SR_1$, wherein $R_1$ is H or $C_1$–$C_4$ alkyl;

is a double-bond between $Y_1$ and $Y_2$;

$Y_1$ is CH; and $Y_2$ is C—W—Ar, wherein W is absent (in other words, a covalent bond), O, S, $NR_2$, SO, $SO_2$, CO, CHOH, $CH_2$, $NR_2CH_2$, $CH_2NR_2$, $NR_2(CO)$, or $(CO)NR_2$, wherein $R_2$ is H or $C_1$–$C_4$ alkyl, Ar is a phenyl substituted at the 3- and 4-positions relative to W, with $R_3$ and $R_4$, respectively, wherein $R_3$ is selected from $NHR_a$, COOH, —COO($C_1$–$C_6$ alkyl), (phenyl)$C_1$–$C_6$ alkoxy, —NH(CO)($C_1$–$C_6$ alkyl), nitro, and amino-$C_1$–$C_6$ alkyl-, wherein $R_a$ is H, $C_1$–$C_4$ alkyl, $C_3$–$C_8$ cycloalkyl, phenyl, or a heterocyclic radical selected from the group consisting of: furyl, oxazolyl, isoxazolyl, thienyl, thiazolyl, pyrrolyl, imidazolyl, triazolyl, tetrazolyl, thiazolyl, oxazolyl, pyridyl, pyrimidyl, triazinyl, pyrazinyl, pyridazinyl, indolyl, pyrazolyl, quinolyl, isothiazolyl, piperidinyl, morpholinyl, piperazinyl, tetrahydrofuryl, pyrrolidinyl, octahydroindolyl, octahydrobenzothiofuranyl, and octahydrobenzofuranyl, benzyl, —$CH_2$-(a heterocyclic radical selected from the group consisting of: furyl, oxazolyl, isoxazolyl, thienyl, thiazolyl, pyrrolyl, imidazolyl, triazolyl, tetrazolyl, thiazolyl, oxazolyl, pyridyl, pyrimidyl, triazinyl, pyrazinyl, pyridazinyl, indolyl, pyrazolyl, quinolyl, isothiazolyl, piperidinyl, morpholinyl, piperazinyl, tetrahydrofuryl, pyrrolidinyl, octahydroindolyl, octahydrobenzothiofuranyl, and octahydrobenzofuranyl, or -M-T, wherein M is sulfonyl, $SO_2NR_b$, $CONR_b$, $CSNR_b$, or $CSR_b$, wherein $R_b$ is H, $C_1$–$C_4$ alkyl, or a heterocyclic radical selected from the group consisting of: furyl, oxazolyl, isoxazolyl, thienyl, thiazolyl, pyrrolyl, imidazolyl, triazolyl, tetrazolyl, thiazolyl, oxazolyl, pyridyl, pyrimidyl, triazinyl, pyrazinyl, pyridazinyl, indolyl, pyrazolyl, quinolyl, isothiazolyl, piperidinyl, morpholinyl, piperazinyl, tetrahydrofuryl, pyrrolidinyl, octahydroindolyl, octahydrobenzothiofuranyl, and octahydrobenzofuranyl, and T is $C_1$–$C_{18}$ alkyl, phenyl, or a heterocyclic radical selected from the group consisting of: furyl, oxazolyl, isoxazolyl, thienyl, thiazolyl, pyrrolyl, imidazolyl, triazolyl, tetrazolyl, thiazolyl, oxazolyl, pyridyl, pyrimidyl, triazinyl, pyrazinyl, pyridazinyl, indolyl, pyrazolyl, quinolyl, isothiazolyl, piperidinyl, morpholinyl, piperazinyl, tetrahydrofuryl, pyrrolidinyl, octahydroindolyl, octahydrobenzothiofuranyl, and octahydrobenzofuranyl, and $R_4$ is $C_1$–$C_2$ alkoxy, $C_1$–$C_2$ thioalkoxy, hydroxy, halo, or $C_1$–$C_4$ alkyl;

Z is $NR_5$, wherein $R_5$ is H, phenyl($C_1$–$C_4$ alkyl) oxycarbonyl, ($C_1$–$C_4$ alkyl) oxycarbonyl, ($C_3$–$C_8$ cycloalkyl) oxycarbonyl, ($C_3$–$C_8$ cycloalkyl)-($C_1$–$C_4$ alkyl)oxycarbonyl, or ($C_6$–$C_{10}$ aryl)oxycarbonyl;

wherein each alkyl, cycloalkyl, phenyl, benzyl, or heterocyclic radical above is optionally substituted with between 1 and 3 substituents independently selected from halo, $C_1$–$C_4$ alkyl, $C_3$–$C_6$ cycloalkyl, $C_1$–$C_4$ alkenyl, $C_1$–$C_4$ alkynyl, phenyl, hydroxyl, amino, (amino)sulfonyl, N-acetyl, O-acetyl, $C_1$–$C_4$ thioalkyl, $C_1$–$C_4$ alkoxy, $COOR_6$, wherein $R_6$ is H or $C_1$–$C_6$ alkyl, $SO_3Na$, $SO_3H$, $SO_2NH_2$, cyano, $CH_2NH_2$, acetyl, di($C_1$–$C_4$ alkyl)amino, and nitro, wherein each substituent alkyl, cycloalkyl, alkenyl, alkynyl, or phenyl is in turn optionally substituted with between 1 and 3 substituents independently selected from halo, $C_1$–$C_2$ alkyl, hydroxyl, amino, and nitro; or a pharmaceutically acceptable salt thereof.

2. A compound of claim 1, or a pharmaceutically acceptable salt thereof, wherein $Q_4$ is N.

3. A compound according to claim 1 of Formula II or a pharmaceutically acceptable salt thereof.

4. A compound of claim 1, or a pharmaceutically acceptable salt thereof, wherein $Q_3$ is N.

5. A compound according to claim 1 of Formula III or a pharmaceutically acceptable salt thereof.

6. A compound of claim 1, or a pharmaceutically acceptable salt thereof, wherein $Q_2$ is N.

7. A compound according to claim 1 of Formula IV

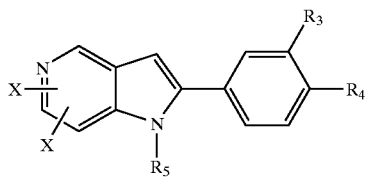

or a pharmaceutically acceptable salt thereof.

8. A compound of claim 1, or a pharmaceutically acceptable salt thereof, wherein $Q_1$ is N.

9. A compound according to claim 1 of Formula V

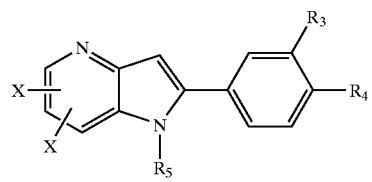

or a pharmaceutically acceptable salt thereof.

10. A compound of claim 1, or a pharmaceutically acceptable salt thereof, wherein $R_a$ or $R_b$ is a heterocyclic radical selected from 3-pyridyl, 3-picolinyl, 2-thienyl, 3-thienyl, 8-quinoyl, and imidazolyl.

11. A compound of claim 1, or a pharmaceutically acceptable salt thereof, wherein $R_a$ or $R_b$ is one of said phenyl, benzyl, alkyl, heterocyclic radical, or a $C_3$–$C_8$ cycloalkyl substituted with at least one substituent selected from halo, hydroxyl, amino, (amino)sulfonyl, N-acetyl, O-acetyl, $C_1$–$C_4$ thioalkyl, $C_1$–$C_4$ alkoxy, $COOR_6$, $SO_3Na$, $SO_3H$, $SO_2NH_2$, cyano, $CH_2NH_2$, acetyl, di($C_1$–$C_4$ alkyl)amino, trifluoromethyl, and nitro and wherein W is a covalent bond.

12. A compound of claim 11, or a pharmaceutically acceptable salt thereof, wherein said substituent is $CO_2R_6$, N-acetyl, di($C_1$–$C_4$ alkyl)amino, hydroxy, halo, or trifluoromethyl.

13. A compound of claim 1, or a pharmaceutically acceptable salt thereof, wherein $R_a$ is a phenyl or benzyl having a substituent in the 3- or 4-position, substituents in the 3- and 5-positions, or substituents in the 3- and 4-positions.

14. A compound of claim 1, or a pharmaceutically acceptable salt thereof, wherein $R_a$ is $C_1$–$C_4$ alkylsulfonyl or $C_{10}$–$C_{14}$ alkylsulfonyl.

15. A compound of claim 1, or a pharmaceutically acceptable salt thereof, wherein $R_4$ is methoxy, hydroxy, or thiomethoxy.

16. A compound of claim 1, or a pharmaceutically acceptable salt thereof, wherein $R_4$ is methoxy.

17. A compound of claim 1, or a pharmaceutically acceptable salt thereof, wherein $R_5$ is H.

18. A compound of claim 1, or a pharmaceutically acceptable salt thereof, selected from the group consisting of:

Thiophene-2-sulfonic acid [2-methoxy-5-(1H-pyrrolo[2,3-b]pyridin-2-yl)-phenyl]-amide;

[2-Methoxy-5-(1H-pyrrolo[2,3-b]pyridin-2-yl)-phenyl]-pyridin-3trifluoromethyl-amine;

[2-Methoxy-5-(1H-pyrrolo[2,3-b]pyridin-2-yl)-phenyl]-pyridin-3trifluoromethyl-phenyl)-amine;

3-{[2-Methoxy-5-(1H-pyrrolo[2,3]pyridin-2-yl)-phenylamino]-methyl}-phenol;

1-(3,5-Dichloro-phenyl)-3-[2-methoxy-5-(1H-pyrrolo[2,3-c]pyridin-2-yl)-phenyl]-thiourea;

1-(3,5-Dichloro-phenyl)-3-[2-methoxy-5-(1H-pyrrolo[2,3-b]pyridin-2-yl)-phenyl]-thiourea;

Thiophene-2-sulfonic acid [2-methoxy-5-(1H-pyrrolo[2,3-c]pyridin-2-yl)-phenyl]-amide;

[2-Methoxy-5-(1H-pyrrolo[2,3-c]pyridin-2-yl)-phenyl]-pyridin-3-ylmethyl-amine;

[2-Methoxy-5-(1H-pyrrolo[2,3-c]pyridin-2-yl)-phenyl]-(3-trifluoromethyl-phenyl)-amine, 3-{[2-Methoxy-5-(1H-pyrrolo[2,3-c]pyridin-2-yl)-phenylamino]-methyl}-phenol;

1-(3,5-Dichloro-phenyl)-3-[2-methoxy-5-(1H-pyrrolo[3,2-c]pyridin-2-yl)-phenyl]-thiourea Thiophene-2-sulfonic acid [2-methoxy-5-(1H-pyrrolo[3,2-c]pyridin-2-yl)-phenyl]-amide;

[2-Methoxy-5-(1H-pyrrolo[3,2-c]pyridin-2-yl)-phenyl]-pyridin-3-ylmethyl-amine;

[2-Methoxy-5-(1H-pyrrolo[3,2-c]pyridin-2-yl)-phenyl]-(3-trifluoromethyl-phenyl)-amine;

3-{[2-Methoxy-5-(1H-pyrrolo[3,2-c]pyridin-2-yl)-phenylamino]-methyl}-phenol;

1-(3,5-Dichloro-phenyl)-3-[2-methoxy-5-(1H-pyrrolo[3,2-b]pyridin-2-yl)-phenyl]-thiourea;

Thiophene-2-sulfonic acid 2-methoxy-5-(1H-pyrrolo[3,2-b]-pyridin-2-yl)-phenyl]amide;

[2Methoxy-5-(1H-pyrrolo[3,2-b]pyridin-2-yl)-phenyl]-pyridin-3-ylmethyl-amine;

[2-Methoxy-5-(1H-pyrrolo[3,2-b]pyridin-2-yl)-phenyl]-(3-trifluoromethyl-phenyl)-amine; and 3-{[2-Methoxy-5-(1H-pyrrolo[3,2-b]pyridin-2-yl)-phenylamino]-methyl}-phenol.

19. A method for treating arthritis, said method comprising administering to patient in need of such treatment a therapeutically-effective amount of a compound of claim 1, or a pharmaceutically acceptable salt thereof.

20. A pharmaceutical composition comprising a therapeutically effective amount of a compound according to claim 1, or a pharmaceutically acceptable salt thereof, together with a pharmaceutically acceptable carrier, excipient, or diluent.

21. A method for treating arthritis, said method comprising administering to patient in need of such treatment a therapeutically-effective amount of a compound of claim 10, or a pharmaceutically acceptable salt thereof.

22. A method for treating arthritis, said method comprising administering to patient in need of such treatment a therapeutically-effective amount of a compound of claim 11, or a pharmaceutically acceptable salt thereof.

23. A method for treating arthritis, said method comprising administering to patient in need of such treatment a therapeutically-effective amount of a compound of claim 14, or a pharmaceutically acceptable salt thereof.

24. A method for treating arthritis, said method comprising administering to patient in need of such treatment a therapeutically-effective amount of a compound of claim 18, or a pharmaceutically acceptable salt thereof.

* * * * *